(12) United States Patent
Alexander et al.

(10) Patent No.: US 11,647,700 B2
(45) Date of Patent: May 16, 2023

(54) METHOD FOR MONITORING GROWTH OF PLANTS AND GENERATING A PLANT GROW SCHEDULE

(71) Applicant: Iron Ox, Inc., San Carlos, CA (US)

(72) Inventors: Brandon Ace Alexander, San Francisco, CA (US); Jonathan Binney, San Francisco, CA (US); Winnie Ding, San Francisco, CA (US); Zachary Wielgosz, San Francisco, CA (US)

(73) Assignee: IRON OX, INC., San Carlos, CA (US)

( * ) Notice: Subject to any disclaimer, the term of this patent is extended or adjusted under 35 U.S.C. 154(b) by 302 days.

(21) Appl. No.: 17/028,641

(22) Filed: Sep. 22, 2020

(65) Prior Publication Data

US 2021/0007287 A1 Jan. 14, 2021

Related U.S. Application Data

(63) Continuation of application No. 15/955,651, filed on Apr. 17, 2018, now Pat. No. 10,813,295.

(Continued)

(51) Int. Cl.
*G06F 7/00* (2006.01)
*A01G 5/00* (2006.01)
(Continued)

(52) U.S. Cl.
CPC .............. *A01G 5/00* (2013.01); *B25J 9/1679* (2013.01); *G01N 33/0098* (2013.01);
(Continued)

(58) Field of Classification Search
CPC .......... A01G 5/00; A01G 7/00; B25J 9/1679; G01N 33/0098; G05B 19/416;
(Continued)

(56) References Cited

U.S. PATENT DOCUMENTS 5,054,831 A 10/1991 Ting et al.
6,327,986 B1 12/2001 Williames
(Continued)

FOREIGN PATENT DOCUMENTS

CN 101406150 A 4/2009
CN 103213128 A 7/2013
(Continued)

OTHER PUBLICATIONS

Extended European Search Report received in EP 17883320.8 dated Jun. 26, 2020.
(Continued)

*Primary Examiner* — Yolanda R Cumbess
(74) *Attorney, Agent, or Firm* — Kilpatrick Townsend & Stockton LLP

(57) ABSTRACT

One variation of a method for monitoring growth of plants within a facility includes: aggregating global ambient data recorded by a suite of fixed sensors, arranged proximal a grow area within the facility, at a first frequency during a grow period; extracting interim outcomes of a set of plants, occupying a module in the grow area, from module-level images recorded by a mover at a second frequency less than the first frequency while interfacing with the module during the period of time; dispatching the mover to autonomously deliver the module to a transfer station; extracting interim outcomes of the set of plants from plant-level images recorded by the transfer station while sequentially transferring plants out of the module at the conclusion of the grow period; and deriving relationships between ambient conditions, interim outcomes, and final outcomes from a corpus of plant records associated with plants grown in the facility.

20 Claims, 4 Drawing Sheets

Related U.S. Application Data

(60) Provisional application No. 62/486,391, filed on Apr. 17, 2017.

(51) Int. Cl.
  *B25J 9/16* (2006.01)
  *G05B 19/416* (2006.01)
  *G06T 7/00* (2017.01)
  *G01N 33/00* (2006.01)

(52) U.S. Cl.
  CPC .......... *G05B 19/416* (2013.01); *G06T 7/0012* (2013.01); *G06T 7/0016* (2013.01); *G05B 2219/39369* (2013.01); *G05B 2219/40233* (2013.01); *G06T 2207/10024* (2013.01); *G06T 2207/30188* (2013.01); *Y10S 901/01* (2013.01); *Y10S 901/47* (2013.01)

(58) Field of Classification Search
  CPC .......... G05B 2219/39369; G05B 2219/40233; G06T 7/0012; G06T 7/0016; G06T 2207/10024; G06T 2207/30188; Y10S 901/01; Y10S 901/47
  USPC .................................................. 700/213, 228
  See application file for complete search history.

(56) References Cited

U.S. PATENT DOCUMENTS

| | | | |
|---|---|---|---|
| 9,538,714 B2* | 1/2017 | Anderson | G06Q 10/06313 |
| 2002/0043195 A1 | 4/2002 | Williames | |
| 2002/0088173 A1 | 7/2002 | Hessel et al. | |
| 2004/0122592 A1 | 6/2004 | Fuessley et al. | |
| 2005/0135912 A1 | 6/2005 | Schempf et al. | |
| 2006/0213167 A1 | 9/2006 | Koselka et al. | |
| 2013/0110341 A1 | 5/2013 | Jones et al. | |
| 2013/0333600 A1 | 12/2013 | Struijk et al. | |
| 2014/0316557 A1 | 10/2014 | Jones et al. | |
| 2016/0050852 A1 | 2/2016 | Lee | |
| 2016/0120114 A1 | 5/2016 | Tsutsumi et al. | |
| 2017/0223947 A1 | 8/2017 | Gall et al. | |
| 2018/0092304 A1 | 4/2018 | Moore | |
| 2018/0343810 A1* | 12/2018 | Counne | A01G 9/022 |
| 2019/0023396 A1* | 1/2019 | Hackert | B64C 39/024 |
| 2020/0012852 A1* | 1/2020 | Ding | G06V 20/00 |
| 2020/0184153 A1* | 6/2020 | Bongartz | A01G 9/249 |

FOREIGN PATENT DOCUMENTS

| | | |
|---|---|---|
| CN | 105265302 A | 1/2016 |
| CN | 103279760 B | 10/2016 |
| EP | 3557970 A4 | 7/2020 |
| JP | 2012191903 A | 10/2012 |
| NL | 1031686 C2 | 10/2007 |
| WO | 2013186669 A1 | 12/2013 |
| WO | 2015110268 A1 | 7/2015 |
| WO | 2016070196 A1 | 5/2016 |

OTHER PUBLICATIONS

Extended European Search Report received in EP 18728818.6 dated Jun. 26, 2020.

International Search Report received in PCT/US18/13807 dated May 16, 2018.

International Search Report received in PCT/US2017/068224 dated Dec. 22, 2017.

Office Action received in CN 201780087239.9 dated Aug. 26, 2021.

Office Action received in EP 18738818.6 dated Mar. 11, 2021.

Office Action received in U.S. Appl. No. 15/872,299 dated Apr. 29, 2020.

* cited by examiner

METHOD FOR MONITORING GROWTH OF PLANTS AND GENERATING A PLANT GROW SCHEDULE

CROSS-REFERENCE TO RELATED APPLICATIONS

This application is a continuation of U.S. patent application Ser. No. 15/955,651, filed on 17 Apr. 2018, which claims the benefit of U.S. Provisional Application No. 62/486,391, filed on 17 Apr. 2017, which is incorporated in its entirety by this reference.

This application is related to U.S. patent application Ser. No. 15/852,749, filed on 22 Dec. 2017, and to U.S. patent application Ser. No. 15/872,299, filed on 16 Jan. 2018, both of which are incorporated in their entireties by this reference.

TECHNICAL FIELD

This invention relates generally to the field of agricultural implements and more specifically to a new and useful method for monitoring growth of plants and generating a plant grow schedule in the field of agricultural implements.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
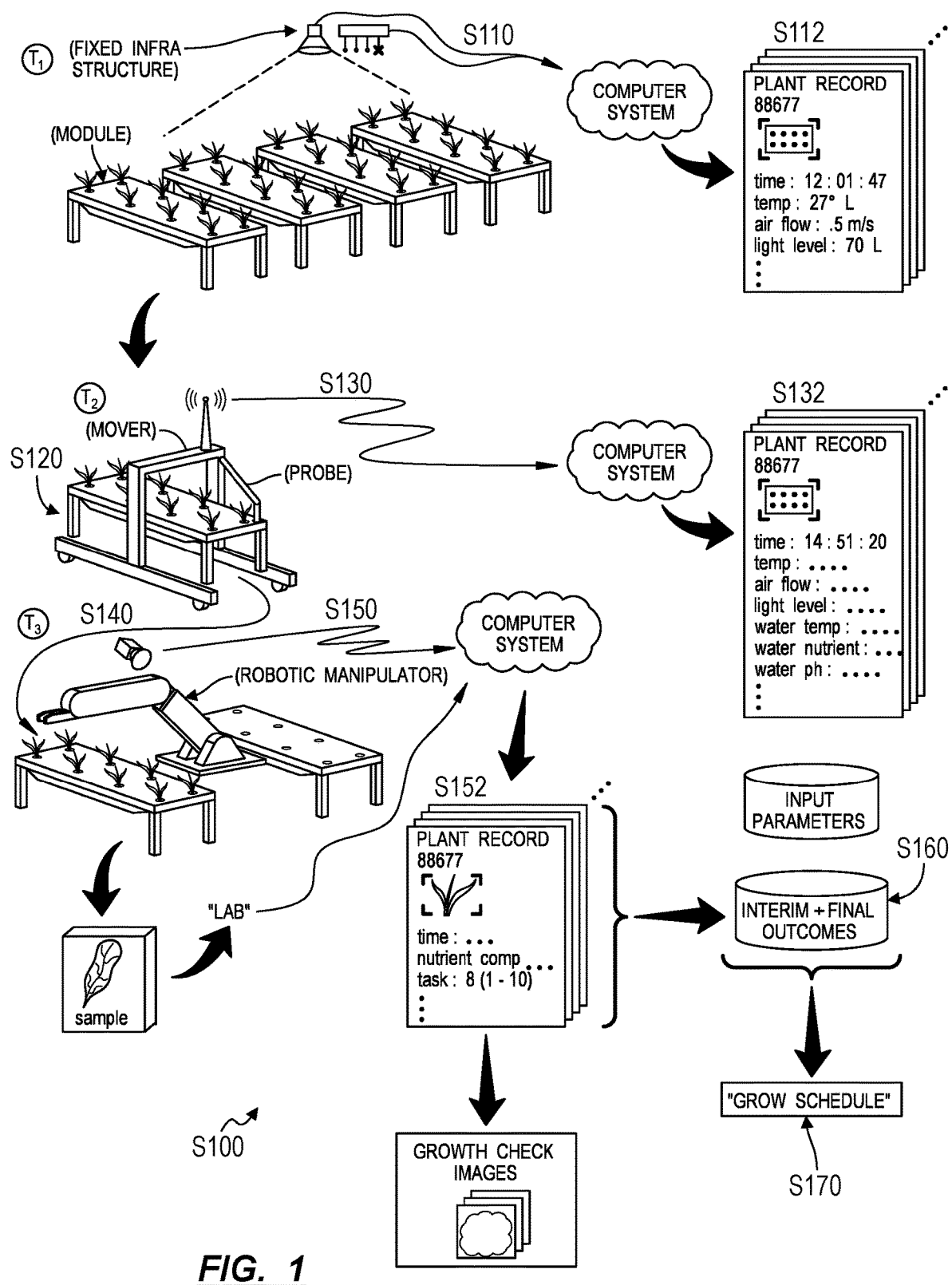
FIG. 1 is a flowchart representation of a method.

As shown in FIG. 1, a method S100 for monitoring growth of plants includes: collecting a first set of images and a first set of ambient data over a group of modules through a set of fixed sensors at a first rate and at a first resolution in Block S110, each module in the group of modules housing multiple plants; writing data from the first set of images and the first set of ambient data to plant records assigned to plants occupying the group of modules in Block S112; navigating a mover to a first module in the group of modules, the mover including a set of mobile sensors in Block S120; collecting a second set of images and a second set of ambient data over the first module through the set of mobile sensors at a second rate and at a second resolution in Block S130, the second rate less than the first rate, the second resolution greater than the first resolution; writing data from the second set of images and the second set of ambient data to plant records assigned to plants occupying the first module in Block S132; delivering the first module to a transfer station in Block S140; while transferring plants from the first module, collecting a third set of images at a third rate and at a third resolution in Block S150, each image in the third set of images representing a plant occupying the first module, the third rate less than the second rate, the third resolution greater than the second resolution; writing data from the third set of images to plant records assigned to plants occupying the first module in Block S152; determining outcomes of plants in the first module based on the third set of images in Block S160; calculating a set of relationships between ambient data and outcomes stored in plant records in Block S170; and generating a grow schedule for new plants loaded into the group of modules based on the set of relationships between ambient data and outcomes in Block S172.

One variation of the method includes: accessing a series of global ambient data recorded by a suite of fixed sensors, arranged proximal a grow area within the facility, at a first frequency during a first period of time in Block Silo; writing global ambient data to plant records associated with plants occupying a group of modules within the grow area based on known locations of modules within the grow area and known locations of plants within the group of modules during the first period of time in Block S112; dispatching a mover to autonomously navigate to the group of modules during the first period of time in Block S120; accessing a series of module-level images of a first module, in the group of modules, recorded by the mover at a second frequency less than the first frequency during the first period of time in Block S130; extracting interim outcomes of a first set of plants, occupying the first module, from the series of module-level images and writing interim outcomes of plants in the first set of plants to plant records associated with plants in the first set of plants based on known locations of the first set of plants within the first module during the first period of time in Block S132; dispatching the mover to autonomously deliver the first module to a transfer station in Block S140; for each plant in the first set of plants, accessing a plant-level image of the plant recorded by the transfer station while transferring the plant out of the first module during a second period of time succeeding the first period of time in Block S150, extracting a final outcome of the plant from the plant-level image, and writing the final outcome to a plant record associated with the plant in Block S152; and deriving relationships between ambient conditions, interim outcomes, and final outcomes from a corpus of plant records associated with plants grown in the facility in Block S160.

2. Applications

Generally, the method S100 can be executed by a computer system in conjunction with a greenhouse or other agricultural facility (hereinafter the "facility"): to autonomously collect optical data of plants housed and transferred between growing modules (hereinafter "modules") through various fixed and mobile high-, moderate-, and low-resolution optical sensors within the facility; to autonomously collect ambient data from near these plants over time through a combination of fixed and mobile high- and low-resolution ambient sensors; to collect plant outcome data, such as size, weight, visual appeal, flavor profile (or "taste"), and nutritional composition, for all or select plants when harvested; to amass these optical, ambient, and outcome data in plant-specific data containers (e.g., discrete files or vectors); and to develop a model for predicting outcome of a singular plant at harvest (and during growth cycles) based on ambient conditions around the plant and/or qualities of the plant recorded days, weeks, or months before the plant is harvested.

2.1 Applications: Data Collection from Fixed and Mobile Infrastructure

In particular, the computer system can interface with fixed sensors arranged in the facility—such as a fixed camera arranged overhead a grow area and a small number of fixed temperature, humidity, light level (e.g., UV, infrared, near-infrared, or visible light level), and wind speed sensors arranged in select locations throughout the grow area—to collect relatively low-resolution optical data (e.g., color photographic images) of a group of modules in the grow area and ambient conditions nearby at relatively high frequency (e.g., once per minute), thereby enabling the computer system to monitor high-level visual and ambient conditions of plants in these modules in near-real-time. The computer system can also interface with an autonomous mover that is configured to autonomously navigate to modules throughout the grow area and to record module-specific data of singular adjacent modules through a suite of integrated mobile sensors—such as a mobile camera and mobile temperature, humidity, light level, wind speed, water temperature, pH, and dissolved oxygen sensors; the computer system can collect moderate-resolution optical and ambient data for all plants in one module at moderate frequency (e.g., once per day), thereby enabling the computer system to intermittently monitor visual and ambient conditions of multiple plants in a singular module (e.g., daily). Furthermore, the computer system can interface with a robotic manipulator and/or an optical inspection station at a transfer station at a fixed location within the facility to collect weight data and high-resolution optical data of a singular plant extracted from a module when the mover delivers this module to the transfer station, such as once per two-week interval. The computer system can also selectively flag a subset of plants (e.g., one plant per ten modules) delivered to the transfer station at harvest time for further testing, such as composition or taste testing at an external facility or manual labeling of the plant's visual appeal by a human grower. The computer system can thus interface with fixed infrastructure and mobile infrastructure to collect low-resolution data at high frequency, moderate-resolution data at moderate frequency, high-resolution data at low frequency, and select plant outcome data on a limited basis.

The computer system can then: quickly detect high-level signs of complications in a subset of modules in the grow area (e.g., wilting, chemical burns) from these low-resolution data; regularly (e.g., daily) detect lower-level signs of complications (e.g., signs of pests, chemical burns) and general plant characteristics within a singular module from these moderate-resolution data; and intermittently detect plant-specific complications and plant-specific characteristics from these high-resolution data. The system can also bolster plant outcome data with selective testing of individual plants.

The computer system can therefore monitor plants across groups of modules, sets of plants in singular modules, and singular plants growing within a facility—containing thousands or millions of plants in various stages of growth at any instant in time—based on data collected by limited fixed and mobile infrastructure deployed within the facility, thereby balancing reaction times to complications, value of individual plants at various stages of growth, cost of infrastructure, and cost of third-party plant testing.

2.2 Applications: Grow Schedule

The computer system can then compile these input and output data into a model that links certain inputs—such as air temperature, humidity, light level, variance of dissolved oxygen, leaf area, leaf color, plant diameter, plant height, etc. over intervals of minutes, hours, days, or weeks—during growth of a plant to the expected outcome—such as visual appeal, size, and taste—of the plant at harvest. The computer system can implement this model to automatically define or adjust growth input parameters realized autonomously by systems throughout the facility while growing new plants in order to drive these new plants toward higher quality, greater visual appeal, greater yield, reduced cost, reduced pest pressures (e.g., due to improved pest detection and mitigation procedures), improved resistance to pests, etc. The system can then autonomously implement these adjusted growth input parameters (e.g., in a revised "grow schedule") for new plants grown at the facility. The system can then repeat these processes over time to collect plant maturation data for these new plants, to collect plant outcome data for these new plants, to refine the model, and to revise growth input parameters for a next batch of plants grown at the facility.

The system can therefore: aggregate input data (e.g., growth input parameters, target ambient conditions) and output data (e.g., size, shape, color, visual appeal, and/or taste at harvest) across a group of plants (e.g., thousands or millions of plants); implement machine learning, artificial intelligence, and/or other statistical techniques (e.g., regression analysis, least square error analysis) to derive correlations between input parameters (e.g., air flow, air temperature, relative humidity, water nutrient level, light level, dissolved oxygen, etc.) and outcomes for these plants; represent these correlations in a model; define target values and tolerance ranges for various input parameters based on correlations with various outcomes represented in this model; and generate a temporal grow schedule that, when implemented for new plants grown in the facility, is predicted to yield certain target plant outcomes (e.g., a combination of target plant size, color, nutrient composition, and flavor profile, etc.).

2.3 Applications: Single Plant Outcome Prediction

Furthermore, the system can track development of an individual plant in the facility over time based on features extracted from low-, moderate-, and high-resolution images of this plants over time and predict a future outcome of this plant accordingly. For example, the system can: compare images of a new plant to images of previous plants of known outcomes; visually match the new plant to a single previous plant or to a composite representation (e.g., an average) of multiple previous plants of similar outcomes (hereinafter a "previous plant"), and predict the outcome of the new plant based on the outcome of the previous plant that exhibits greatest similarity (or "proximity") to the new plant. The system can then: maintain a current grow schedule for the plant (and other plants in the same module) if the known outcome is positive; cull the plant (e.g., upon next delivery by the mover to the transfer station) if the known outcome is negative; or identify a second previous plant associated with a positive outcome but exhibiting visual similarities with the new plant at approximately the same stage of development and shift the grow schedule of the new plant toward the grow schedule realized for the second plant in order to improve likelihood of a positive outcome for the new plant.

2.4 Infrastructure and Plant Flow

Figure 4:
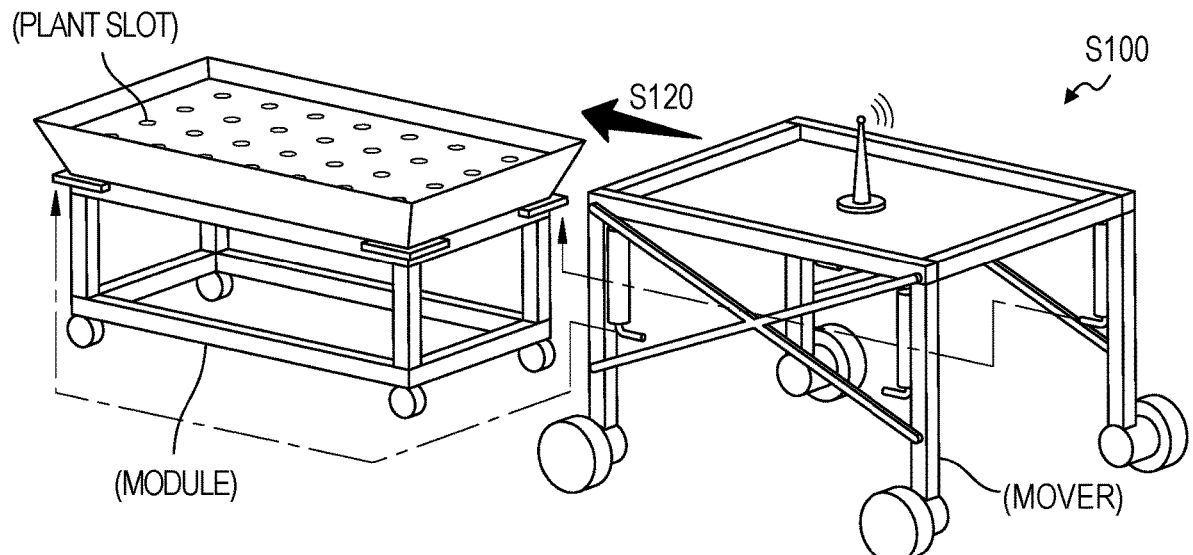
FIG. 4 is a flowchart representation of one variation of the method.
Figure 5:
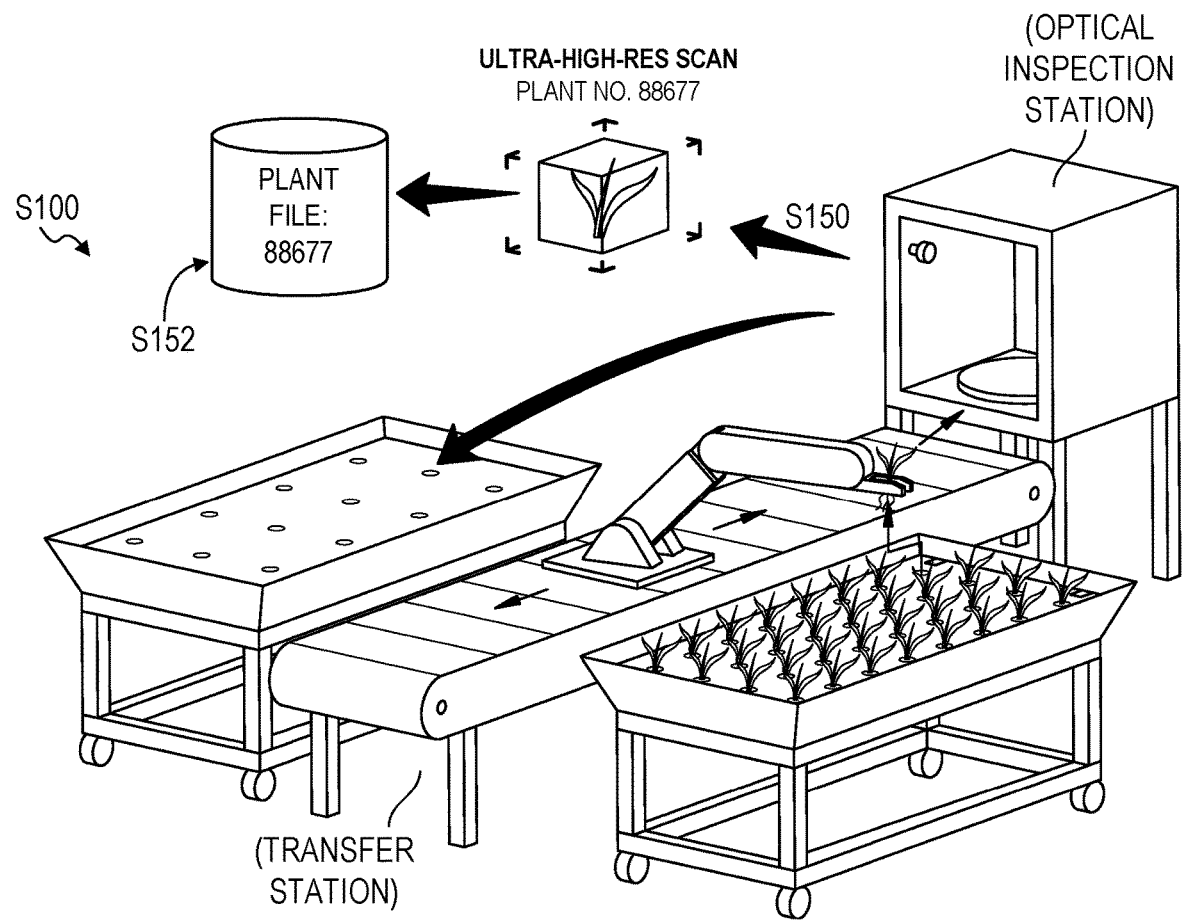
FIG. 5 is a flowchart representation of one variation of the method.

As shown in FIGS. 1, 4, and 5, the method S100 can be executed by a system, such as including: a local or remote computer system (e.g., a remote server); a robotic manipulator connected to the computer system, located at a transfer station within the facility, and outfitted with a camera, scale, and/or end effector configured to retrieve plants from modules; and/or an autonomous "mover" configured to autonomously navigate throughout the facility, to record data (e.g., optical, ambient, and/or contact-based data) of individual modules, to deliver modules to the transfer station responsive to commands issued by the computer system, and to return modules to their assigned locations throughout the facility.

In particular, plants may be grown in modules containing a growing tray and defining an array of plant slots configured to hold one plant (or a "bunch" of like plants, such as multiple basil plants). Young plants (or "seedlings") may have relatively small leaves covering a relatively small area such that these young plants require only a small grow volume; as these plants mature (e.g., to a "sapling" stage or through "thinning" and "rosette" stages"), their leaves may grow to cover a greater area, thereby requiring a larger grow volume; as these plants mature further (e.g., through "early-heading," "mid-heading" and "mature-heading" stages"), their leaves may develop more fully to cover a greater area up to harvest, thereby necessitating an even larger grow volume. In order to maintain a relatively high throughput per floor area within the facility, the facility can be outfitted with modules of different types—that is, modules with different plant slot densities suited to various stages of plant growth and therefore to various size ranges of plants from seeding to harvest. For example, the facility can be outfitted with: seeding trays (or "seeding modules") defining a highest density of plant slots (e.g., 640 plant slots per 4-foot by 12-foot module) and configured to hold plants during a seedling stage; modules of a first type (hereafter a "nursery type") defining a moderate density of plant slots (e.g., plant slots per 4-foot by 12-foot module) and configured to hold plants during a sapling stage; and modules of a second type (hereinafter a "finishing type") defining a lowest density of plant slots (e.g., 40 plant slots per 4-foot by 12-foot module) and configured to hold plants during a finishing stage and up to harvest. By placing young plants first in modules with greatest plant slot densities and then transiting these plants to modules characterized by lower and lower plant slot densities as the plants increase in size and maturity, the facility can house and grow more plants per module on average and therefore achieve greater space efficiency (i.e., a number of plants per floor area within the facility).

As modules—and plants occupying these modules—are stationed and repositioned throughout the facility over time, various fixed and mobile sensors within the facility can collect general, module-specific, and plant specific ambient data, water quality data, and optical data. The system can then: merge these data to derive correlations between ambient conditions, water qualities, and visual characteristics of plants and their eventual outcomes; and develop grow schedules for future plants grown in the facility in order to achieve certain outcomes.

3. System

The method S100 can be executed by a system including: a computer system; a fixed sensor suite; an automated (or "autonomous") mover; and a robotic manipulator. The fixed sensor suite is connected to the computer system and is configured to regularly collect optical data (e.g., overhead digital photographic images) of multiple modules—each containing multiple plants—and to collect ambient sensor data from over these modules, such as once per hour or once per second. The mover is connected to the computer system and configured: to navigate to single modules throughout the facility; to collect optical data from groups of plants in a single module and to collect water quality data from these modules, such as once per day or every other day; and to deliver single modules to a transfer station and to return modules to their assigned locations throughout the facility, such as once per two-week interval per module. The robotic manipulator is connected to the computer system, is located at a transfer station within the facility, and is configured to collect optical, weight, and/or other data from individual plants while moving plants between modules, such as from a nursery module to a finishing module.

In particular, the mover can be configured to automatically navigate throughout the facility to a particular location under or near a module, to couple to or lift the module, to navigate—with the module—to a transfer station within the facility, and to release (or "deposit") the module at the transfer station. While moving past other modules on its way to collecting a particular module for delivery to the transfer station, the mover can also collect optical and water quality data from these other modules. The robotic manipulator can be arranged near the center of the transfer station, and the mover can arrange a first module of a nursery type (e.g., containing a high density of plant slots) and a second module of a finishing type (e.g., containing a lower density of plant slots) adjacent the robotic manipulator at the transfer station in order to enable the robotic manipulator to navigate its end effector across both the full extent of plant slots in the first module and the full extent of plant slots in the second module. The mover can also deposit a third module of the finishing type to the transfer station, such as adjacent the second module, and the robotic manipulator can transition to transferring cleared plants from the first module to the third module once all plant slots in the second module are filled. The mover can then return the second and third modules to assigned grow areas within the facility, such as under a translucent roof and/or under artificial lighting.

The mover can also deliver a seeding tray to the transfer module, and the robotic manipulator can implement similar methods and techniques to check sizes and weights of plants in the seeding tray and to sequentially transfer plants from the seeding tray into the first module before the mover returns the first module to an assigned grow area within the facility. Alternatively, the system can include a second robotic manipulator arranged at a second transfer station within the facility, and the mover can deliver the first module and the seeding tray to the second transfer station, and the second robotic manipulator can transfer seedlings from the seeding tray into the first module.

Similarly, the (first) robotic manipulator at the (first) transfer station, the second robotic manipulator at the second transfer station, or a third robotic manipulator at a third transfer station within the facility can remove plants from the second and third modules of the finishing type (e.g., for manual or automated processing, such as removal of roots) and/or place plants from the second and third modules into packages (e.g., boxes, pallets) for distribution from the facility.

The method S100 is described below as executed by the system: to collect low-resolution plant related-data at a high frequency through fixed infrastructure (i.e., a fixed sensor suite) within the facility; to collect moderate-resolution plant related-data at a moderate frequency through mobile infrastructure (i.e., a mobile sensor suite on the mover); to collect high-resolution plant related-data at a low frequency through a single plant manipulator (e.g., the robotic manipulator); while also autonomously moving plants from modules containing high densities of plant slots to modules containing lower densities of plant slots to accommodate growth of these plants over time. The computer system executing Blocks of the method S100 can then: selectively write these optical and numerical-point data to plant records assigned to each individual plant; collect final results of these plants, such as nutrient values, flavor profile, and visual appeal; and extrapolate combinations and ranges of inputs that yield maximum, target, or sufficient compromises of nutrient values, flavor profile, grow time, and cost, etc.

The method S100 is also described as executed by the system to automatically transfer lettuce through a sequence of seeding trays, nursery-type module, and finishing-type modules. However, the method S100 can be implemented in a greenhouse or other facility in conjunction with growing any other type of plant, such as fruit, vegetables, legumes, flowers, shrubs, or trees, etc.

4. Modules

The system includes a set of modules configured to house a group of plants throughout a segment of the growth cycle of these plants (e.g., four weeks of a twelve-week grow-period). Each module can define a standard size (e.g., four feet in width by eight feet in length by four feet in height; two meters in width by five meters in length by one meter in height) and can include a number of plant slots matched to the segment of plant growth cycle associated with the module. For example: a seeding-type module can include 192 plant slots; a nursing-type module can include 48 plant slots (i.e., one-quarter as many as seeding-type modules); and a finishing-type module can include twelve plant slots (i.e., one-quarter as many as nursing-type modules); as shown in FIG. 5, despite these modules defining the same overall size and geometry.

4.1 Hydroponic Trays

In one implementation, a module includes: a set of hydroponic trays (or hydroponic tubes), each defining a (linear) array of plant slots, wherein each plant slot is configured to receive and retain one plant (or one cluster of multiple plants); a carriage or frame supporting the set of hydroponic trays at an angle, such as declining 5° from horizontal; a reservoir fluidly coupled to the set of hydroponic trays and configured to collect water flowing out of the hydroponic trays; and a pump configured to cycle water from the reservoir back through the set of hydroponic trays. The module can additionally or alternatively be configured to transiently connect to a water supply line and to a water return line in the facility, which can provide a constant supply of water and nutrients to plants in this module. In this implementation, the module can also include: one optical fiducial at the front of each hydroponic tray; optical fiducials at the end of each hydroponic tray; one optical fiducial adjacent each plant slot along each hydroponic tray; or optical fiducials at three or four corners of the modules; etc. The system can thus detect these optical fiducials—such as through optical sensors integrated into the mover and into the robotic manipulator—to identify and locate the module and to locate plant slots in each hydroponic tray in the module.

4.2 Open Trays

In another implementation shown in FIGS. 4 and 5, a module includes: an open tray configured to contain a standing volume of water and nutrients; a cover arranged over the open tray and including a set of perforations, wherein each perforation defines a plant slot configured to receive and retain one plant (or one cluster of plants); and a stand configured to support the tray off of the ground. In the implementation: the open tray can define a standard rectangular geometry, as described above; and the lid can include a rectangular cover configured to float in water in the tray. For example, the lid can include: a rigid panel (e.g., nylon or aluminum sheet) defining an array (e.g., a linear grid array, a close-pack array) of plant slots; and floats extending across the underside of the rigid panel and exhibiting sufficient buoyancy and/or height to maintain an air gap between the top surface of water in the tray and the bottom surface of the lid when the array of plant slots in the lid are filled with plants, thereby maintaining exposure to air—and therefore oxygen—for upper root systems of these plants. Furthermore, in this example, because the lid floats on the water in the tray, the lid can ensure that roots of these plants remain in contact with water in the tray despite changes to the water level in the tray.

Furthermore, in this implementation, the module can include a set of optical fiducials arranged on the top surface of the lid and/or the tray and configured to indicate position, orientation, distance, type, and/or unique identity of the module. For example, the module can include: one optical fiducial (e.g., a unique barcode or quick-response code) arranged at each of three or four corners on the lid; three (identical) colored dots (e.g., yellow for nursery stage, red for finishing stage) arranged at corners of the lid or tray; or one optical fiducial adjacent each plant slot on the lid (e.g., a colored circle, square, or polygon of known geometry and dimension encircling each plant slot); etc.

Alternatively, the module can include an open tray with a fixed lid. In this implementation, the tray and fixed lid can define geometries and features similar to those in the foregoing implementation but with the lid fixedly coupled to the rim of the tray, such as sealed against the rim of the tray to prevent water from splashing out of the tray when the module is moved by the mover.

However, a module can define any other structure or geometry and can define any other number or arrangement of plant slots.

5. Fixed Infrastructure

As shown in FIG. 1, the system can include a fixed optical sensor (e.g., a color camera) arranged in a fixed location over modules in the facility and configured to regularly record images of multiple plants across multiple modules below. For example, the fixed optical sensor can be mounted to the ceiling of the facility or coupled to artificial (e.g., backup) lighting arranged over a grow area within the facility.

The system can also include a suite of fixed ambient sensors, such as including: an air speed sensor; a relative humidity sensor; a temperature sensor; and a light level sensor. For example, the suite of fixed ambient sensors can be arranged adjacent the fixed overhead camera over a grow area of the facility. The system can additionally or alternatively include multiple fixed suites of ambient sensors arranged throughout the grow area, such as suspended from ceiling or mounted on load-bearing columns within the facility and such as including one suite of fixed ambient sensors per square meters of grow area.

5.1 Data Collection

The fixed optical sensor can regularly record images of the grow area below; and sensors in the suite of fixed ambient sensors can regularly collect ambient data. For example, the fixed optical sensor can record an image of once per 10-minute interval; the suite of fixed ambient sensors can record air speed, humidity, air temperature, and light level values once per second; and the fixed optical sensor and the suite of fixed ambient sensors can return these data to the computer system via a wired or wireless connection.

5.2 Data Extraction from Global Image

Generally, because the field of a view of the fixed optical sensor contains the entirety of the grow area or a large portion of the grow area housing multiple modules, wherein each module is occupied by the multiple individual plants, the per-plant resolution of an image recorded by the overhead camera may be relatively minimal. For example, for a four-megapixel optical sensor defining a field of view over a ten-meter by ten-meter portion of the grow area housing a 4×8 grid array of two-meter by one-meter modules, each of these modules occupied by a 4×12 array of plants at a nursery stage of development, a single plant in an image recorded by the fixed optical sensor may be represented in a relatively small 20-pixel by 20-pixel region of this image, which may be insufficient to detect pests or calculate a size of the individual plant with a high degree of accuracy.

However, the system can extract higher-level visual information from this image, such as generally whether multiple plants occupying a module are experiencing chemical burns, are overexposed to light, or are wilting. For example, upon receipt of an image from the fixed optical sensor, the system can: implement computer vision techniques to detect a floor area represented in the image (e.g., represented by dark pixels or background pixels in the image); remove the floor area from the image; implement computer vision techniques (e.g., edge detection) to detect and distinguish discrete modules in the remaining region(s) of the image (e.g., represented by white and near-white pixels in the image; and scan the remaining region(s) of the image for "green," "brown," and "yellow" pixels. The system can then: label "green" pixels within a known "healthy" green color range as representing healthy plant matter; label "green" pixels within a known "sub-healthy" green color range as representing unhealthy plant matter; and label "brown" and "yellow" pixels as representing damaged or dead plant matter. For each module detected in the image, the system can: associate "green," "yellow," and "brown" pixels located within the detected perimeter of the module with this module; estimate an average size of plants in the module based on a ratio of the number of pixels labeled as plant matter to a total number of pixels within the bounds of the module; and estimate a proportion of unhealthy plant matter in the module based on a ratio of a sum of pixels labeled unhealthy, damaged, and dead plant matter to a total number of pixels labeled as plant matter within the bounds of the module.

For each module, the system can then compare this estimate of average plant size derived from the current image recorded by the fixed optical sensor to estimates of average plant size derived from similar regions of preceding images recorded by the fixed optical sensor (over a period of time in which the module was not known to have been moved by the mover) to determine whether the average size of plants in the module has increased or decreased; if the system determines that the average size of plants in the module thus derived from this series of images has decreased, the system can flag the module as containing wilting plants. The system can similarly compare a proportion of unhealthy plant matter in the module estimated from the current image recorded by the fixed optical sensor to proportions of unhealthy plant matter estimated from similar regions of preceding images recorded by the fixed optical sensor to determine whether the proportion of unhealthy plant matter in the module is increasing or decreasing; if the system determines that the proportion of unhealthy plant matter in the module thus derived from this series of images has increased, the system can flag the module as overexposed (e.g., overexposed to light, heat, humidity, pH, or nutrients).

The system can therefore extract low-resolution visual information characterizing the health and changes in the health of many plants occupying many modules in the field of view of the fixed optical sensor from images thus recorded by the fixed optical sensor.

5.3 Plant Association of Fixed-Infrastructure Data

The system can then associate these ambient and image-derived data with specific plants known to be in modules within the grow area.

Figure 2:
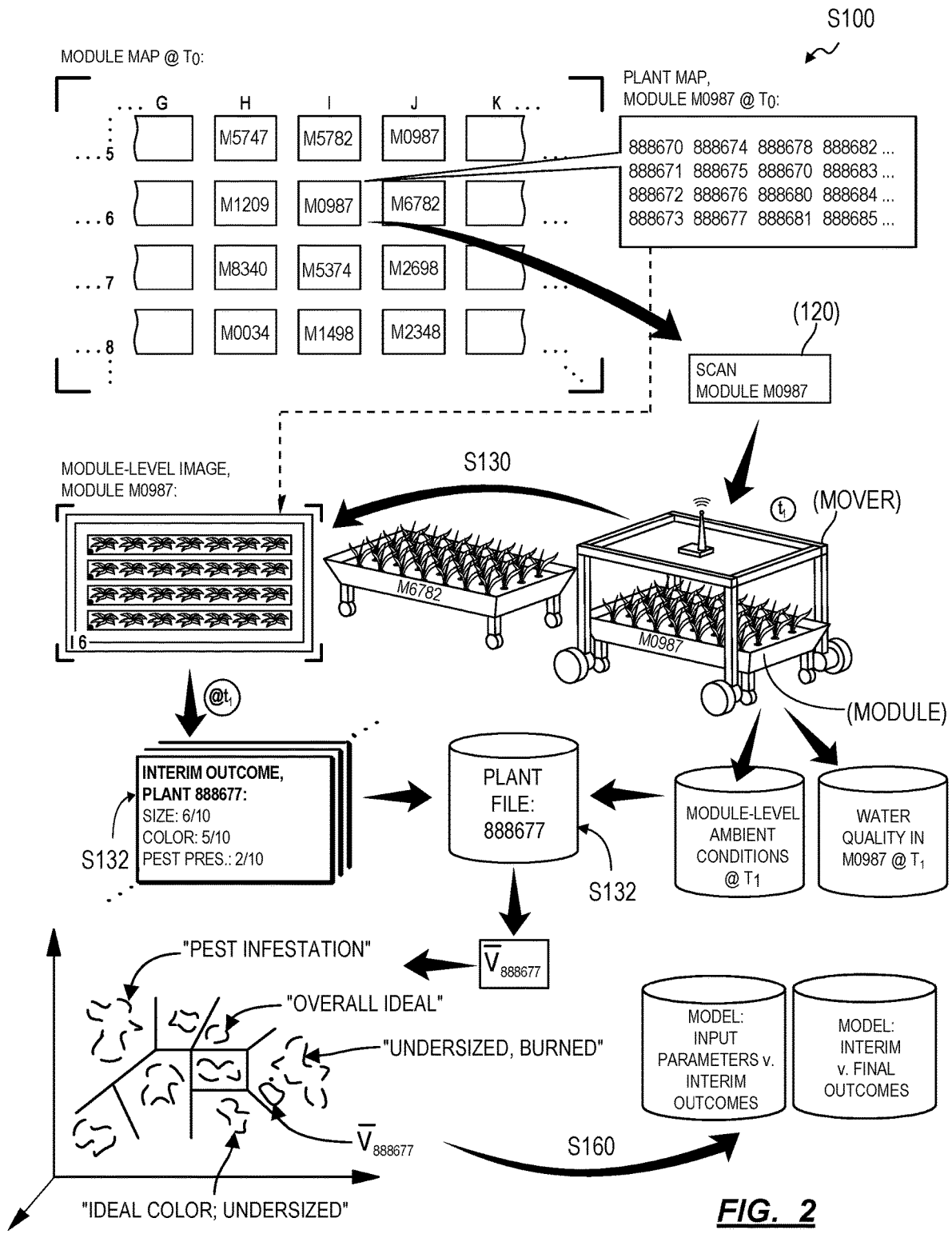
FIG. 2 is a flowchart representation of one variation of the method.

In one implementation shown in FIG. 2, the system maintains a module map of last known locations of modules throughout the facility (e.g., a current (x,y) location of each module within a coordinate system defined for the facility); as the mover moves a particular module throughout the facility, such as according to a command issued by the system, the system can update this module map with new locations of this particular module (e.g., in real-time) based on locations returned by the mover during this transfer. Upon receipt of an image from the fixed optical sensor, the system can: dewarp the image; implement computer vision techniques to segment the image into regions representing discrete modules in the grow area, as described above; calculate an (x,y) location of the center of each image segment based on a known position and orientation of the fixed optical sensor within the facility (or based on fixed fiducials detected in a region of the image representing a floor of the facility); and then, for each image segment, associate the image segment with an identifier of a particular module based on proximity of the image segment to the last known location of this particular module stored in the module map.

The system can also maintain: one unique plant record for each plant occupying a module in the facility, such as in the form of a multi-dimensional vector as described below and shown in FIG. 2; and a plant map linking each unique plant record to an identifier of a module and an address of a plant slot—in this module currently occupied by the corresponding plant. (As the robotic manipulator at the transfer station moves a plant from one plant slot in one module to a plant slot in another module or into a harvest container, etc., the system can update this plant map accordingly.) For a particular module identified in the current image recorded by the fixed camera, the system can write a timestamp, an average plant size, a ratio of unhealthy to total plant matter, a change in size or health of plants, and/or any other quantitative data extracted from the image to each plant record of plants known to occupy this module according to the plant map.

Alternatively, the system can detect optical fiducials on a module detected in an image received from the fixed optical sensor and align a preexisting slot map for a type of the module to these optical fiducials to locate approximate centers of each plant slot—and therefore each plant—in the module. For each plant slot thus detected for this module, the system can: associate a cluster of pixels in the image around this plant slot with a plant; implement the foregoing methods and techniques to derive a size, health, change in size, and/or change in health, etc. of a plant occupying this plant slot based on colors of pixels in this cluster of pixels and/or based on differences between pixels in this cluster of pixels and corresponding clusters of pixels in preceding images recorded by the fixed optical sensor; and write these plant-specific values to the plant record associated with this plant slot by the plant map.

The system can similarly write timestamped ambient sensor data received from the suite of fixed ambient sensors to plant records assigned to plants known to be proximal these sensors (i.e., based on the module map and the plant map).

However, because fixed ambient sensors may be substantially remote from a module, global ambient sensor data collected by the suite of fixed ambient sensors may loosely represent ambient conditions immediately adjacent plants occupying this module. Therefore, in one variation described below, the system can calculate a temperature correction gradient that transforms a single air temperature value read by a fixed temperature sensor in the suite of fixed ambient sensors into temperatures at locations across the grow area—such as a function of time of day and/or time of year—based on temperature data collected by the mover while traversing the grow area over time. Upon receipt of a new temperature value from the fixed transfer station, the system can: input this new temperature value (and a current time of day and/or time of year) into the temperature correction gradient to estimate a current temperature gradient across the grow area; project known locations of modules from the module map (or locations of specific plants based on the module map and the plant map) onto the temperature gradient estimated for the grow area to estimate a temperature at each module (or at each individual plant) within the grow area; and write these estimated temperature values to corresponding plant records. The system can implement similar methods and techniques to develop and implement air speed, humidity, and/or light level correction gradients and to estimate air speed, humidity, and/or light level values at each module (or at each individual plant) in the grow area based on these correction gradients and new air speed, humidity, and/or light level data received from the suite of fixed ambient sensors.

Therefore, the system can: collect relatively low-resolution ambient sensor data and images of the grow area at a relatively high frequency through static infrastructure deployed within the facility; and regularly populate plant records—assigned to plants represented in these images and occupying modules known to be near these fixed sensors—with these numerical-point data and other data extracted from these images. The system can thus form a dense historical record of low-resolution plant characteristics and low-resolution ambient conditions around a plant for each plant grown in the facility and store these dense historical records in corresponding plant-specific plant records.

(The system can additionally or alternatively include an autonomous aerial drone outfitted with an optical sensor and ambient sensors, as described above, and configured to navigate throughout the facility, collect images of modules below, and collect ambient sensor data according to similar methods and techniques.)

6. Mover

As described above and shown in FIGS. 2 and 4, the mover defines a vehicle that autonomously: navigates throughout the facility; selectively arranges itself over (or adjacent) modules; collects sensor data from in and around these modules (e.g., images of plants in a module, water quality data of water stored in the module, and/or ambient data around the module); delivers modules to the transfer station for transfer of plants into and out of these modules; and returns these modules to their assigned locations throughout the facility, such as responsive to commands issued by the computer system.

6.1 Autonomous Navigation

As described below, the computer system generates commands to transport specific modules to various locations throughout the facility, such as "module transfer requests" to transport modules between the grow area, transfer station, a cleaning station, a maintenance area, a dosing station, and/or a quarantine station. The computer system can also generate commands to collect optical, ambient, and/or water quality data from specific modules throughout the facility, such as "module scan requests" to record module-level images, local air temperature and humidity, and dissolved oxygen and water temperature in water stored in select target modules. The computer system can distribute these commands to the mover, and the mover can autonomously execute these commands.

In one implementation, the mover includes a gantry or boom. To engage a module, the mover can: navigate to and align itself over the module, such as based on optical fiducials applied to the module; extend the boom into contact with the module; trigger a latch on the boom to engage the module; and then retract the boom to lift the module. Alternatively, modules in the facility can include casters; to engage a module, the mover can navigate up to and align itself with the module, trigger a latch to engage the module, and then push or pull the module—on its casters—to another location within the facility (e.g., to the transfer station) before releasing the latch to disengage the module.

For the mover that is configured to autonomously navigate over a module, the mover can also include a downward-facing optical sensor. As the mover approaches a module, the mover can: detect an optical fiducial—located on the module—in the field of view of the downward-facing optical sensor; and navigate toward the module to locate this optical fiducial in a target position and/or orientation in the field of view of the downward-facing optical sensor in order to align itself to the module before triggering the boom or latch to engage the module. However, the mover can implement any other method or technique to engage and manipulate a module.

6.2 Mobile Water Quality Sensors

The mover can also include a mobile suite of water quality sensors configured to collect various water quality data of water stored in a module.

Generally, water quality sensors may be expensive and require regular calibration, which may increase complexity and cost of collecting such water quality data. The mover can therefore include a single mobile suite of sensors and can collect water quality data from many modules throughout the facility over time, thereby limiting water monitoring infrastructure costs, limiting complexity of calibrating and cleaning these sensors, and distributing costs for these sensors and calibration of these sensors across many modules in the facility over time.

In one example, the mover includes a water temperature sensor, a pH sensor, a nutrient level sensor (e.g., a dissolved oxygen, nitrogen, or other nutrient level sensor), and/or a water level sensor, all arranged on a probe that is mounted to an actuator on the mover. In this example, the probe can be arranged on the mover such that the probe is aligned to an access window on a module (e.g., a spring-loaded window on the cover floating in the open tray of the module) when the mover autonomously aligns itself over this module. Thus, upon arriving at and aligning itself over to a module, the mover can extend the actuator to advance the probe downward, through the window, and into the open tray of the module, thereby bringing these water sensors into contact with water stored in the tray. The mover can then read water quality (and quantity) values from these sensors and upload these data to the computer system (e.g., via a local wireless network).

In one variation, the mover also includes a sanitation block; between retracting the probe from one module and inserting the probe into a next module according to module scan commands received from the computer system, the mover can pass the probe into the sanitation block in order to sanitize the probe, thereby reducing propagation of contaminants (e.g., spread of pests, such as algae) from one module to the next via the probe as the mover navigates from one module to the next. For example, the sanitation block can include a steam chamber, vinegar wash, or UV-light box, and the mover can sanitize the probe after sampling each module in the facility.

The mover can additionally or alternatively include a calibration block containing a calibration fluid of known temperature, pH, and/or nutrient level (e.g., a dissolved oxygen, nitrogen). During operation, the mover can insert the probe into the calibration block and calibrate sensors mounted to the probe according to known qualities of the calibration fluid. For example, the calibration block can include a volume of pH calibration fluid of known pH; after sanitizing the probe in the sanitation block described above, the mover can dry the probe (e.g., with a blast of air), insert the probe into the pH calibration fluid, calibrate the pH sensor to the known pH of the pH calibration fluid, and rinse and dry the probe. The mover can repeat this process once per day, once per measurement of 50 modules, or on any other interval.

6.3 Mobile Ambient Sensors

The mover can also include a mobile suite of ambient sensors configured to collect various ambient data from around a module.

In one implementation, the mobile suite of ambient sensors includes air speed, relative humidity, temperature, and light level sensors, such as mounted to the chassis of the mover at a height that approximates a height of plants growing in modules throughout the facility. In another example, the mobile suite of ambient sensors can be mounted to the probe described above—above the water quality sensors—such that the mobile suite of ambient sensors is located adjacent foliage of plants in a module when the mover lowers the probe into a sampling position over the module.

The mover can then read ambient conditions proximal this module from these ambient sensors and upload these data to the computer system (e.g., via the local wireless network).

Upon receipt of these local ambient data from the mover, the system can: reference the module map and plant map described above to identify plants occupying this module; and then write these local ambient data—and a corresponding timestamp—to plant records associated with each of these plants.

6.4 Mobile Optical Sensor

The mover can also include a mobile optical sensor (e.g., a 2D or 3D color camera, a 2D multispectral camera), such as mounted to the gantry and facing downward such that the full width and length of a module—and substantially all plants occupying the module—fall within the field of view of the mobile optical sensor when the mover is aligned over the module. Thus, upon arriving at a module during execution of a module transfer or module scan request, the mover can record a module-level image of the module below and upload this module-level image to the computer system (e.g., via the local wireless network).

6.5 Data Extraction from Module-Level Image

The system can then extract moderate-resolution visual information of a group of plants occupying a particular module from a module-level image thus recorded by the mobile optical sensor in the mover while the mover interacts with this module.

In one implementation, the system extracts an approximate size (e.g., width, diameter) of each plant in the module from this module-level image. In one example, the system implements computer vision techniques, such as edge detection or blob detection, to: identify a perimeter of the first module in the image; count a number of green pixels in the image (e.g., a number of pixels exceeding a threshold intensity or brightness in the green color channel in the image); and then authorize plants in the first module for transfer to a second module if the ratio of green pixels to a total number of pixels in the image exceeds a threshold ratio. Similarly, the system can implement a color classifier to classify a likelihood that each pixel in the image represents plant matter and then count the number of pixels in the image that are classified as 'likely to represent plant matter.'

The system can implement these methods and techniques for each color channel in the image, merge classifications for corresponding pixels in each color channel, count a number of pixels in a composite color space that are 'likely to represent plant matter,' and identify clusters of pixels 'likely to represent plant matter.' The system can also: detect an optical fiducial in the image; and align a preexisting plant slot map for the known module type of the module (e.g., stored in the module map and confirmed by information stored in the optical fiducial) to these optical fiducials to approximate centers of each plant slot—and therefore each plant—in the module represented in the image. For a first plant slot in the first module thus located in the image, the system can then: identify a cluster (or "blob") of pixels 'likely to represent plant matter' (e.g., a cluster of green pixels exceeding a threshold intensity or brightness in the green color channel in the image) radiating from the approximate center of the first plant slot located in the image; associate this cluster of pixels with a first plant in the first plant slot in the module; and estimate a size (e.g., an approximate diameter) of the first plant based on a size and geometry of this cluster of pixels.

The system can also: implement methods and techniques similar to those described above and below to detect yellow and brown pixels near this cluster of green pixels; and characterize a health of the first plant based on presence of these yellow, brown, or dark pixels. In one example, the system implements template matching or object recognition techniques to identify leaves in the cluster of pixels associated with the first plant in the module-level image, such as based on template images or models of leaves of plants of the same type and at similar growth stages as the first set of plants in the first module. The system can then correlate light-colored (e.g., yellow, tan, brown) regions around perimeters of these leaves with chemical burns or insufficient nutrient supply and estimate a degree of chemical burns in the first plant based on a proportion of light-colored leaf area to green leaf area in the region of the module-level image correlated with the first plant. The system can implement similar methods and techniques to detect indicators of over- or under-exposure to temperature, humidity, light, nutrients, etc. based on presence of brown and yellow pixels and/or the "greenness" of green pixels in this region of the module-level image.

In another example, the system scans the module-level image for dark, discolored leaf regions that may indicate a nematode infestation. In this example, if the system detects any such dark, discolored leaf region in the first module, the system can calculate a proportion of discolored leaf area to healthy leaf area (e.g., brown and yellow pixels to green pixels) in the region of the image representing the first plant. In particular, the resolution of the module-level image may be insufficient to detect insects (e.g., ants, aphids, flies, silverfish, moths, or caterpillars, etc.) or other pests on the first plant directly. However, the system can scan the region of the module-level image associated with the first plant for indicators of pest pressure in the first plant.

However, the system can extract any other characteristics or health indicators for the region of the module-level image thus associated with the first plant in this module.

The system can then: access the module map and plant map described above to identify a particular plant record corresponding to the first plant; write these data derived from the module-level image to the particular plant record; and/or write the segment of the image thus associated with the first plant to the particular plant record.

The system can repeat this process for each other plant slot located in the first module and update corresponding plant records accordingly.

6.6 Module-Level Scan Scheduling

The system can include a single mover (or small set of like movers) configured to navigate to individual modules throughout the facility and to collect optical, water quality, and ambient sensor data at each module according to commands issued by the computer system. For example, the mover can collect ambient data, water quality data, and a module-level image of a module during a module-level scan when the mover reaches the module and before moving the module while executing a module transfer request for this module. In this example, the mover can additionally or alternatively execute a module scan of the module upon delivering the module to the target destination specified in the module transform request. In another example, the mover can collect ambient data, water quality data, and a module-level image of a module during a module-level scan when the mover reaches a module specified in a module scan request; upon collecting these data, the mover can leave this module otherwise undisturbed and move on to a next module in a command queue maintained by the computer system.

Therefore, the mover (or a small set of movers in the facility) can collect module-level data from each module in the facility on a regular basis, such as once per day. Furthermore, though the mover may collect module-level data of an individual module less frequently than fixed infrastructure sensors in the facility, these module-level data may exhibit greater per-plant resolution than general data collected by the infrastructure, thereby enabling the system to extract more sophisticated insights into each plant in the facility from these module-level data (e.g., once per day).

6.7 Sensor Calibration

In one variation, the system calibrates high-frequency data collected by the suite of fixed ambient sensors based on moderate-frequency, higher-resolution ambient data collected by the suite of mobile ambient sensors in the mover. In particular, because the mover locates the suite of mobile ambient sensors immediately adjacent a module when recording module-level ambient data, these module-level ambient data may better represent true temperature, humidity, light level, and/or air flow conditions immediately adjacent plants in this module than ambient data collected by the suite of fixed ambient sensors.

In one implementation, the system calculates a temperature correction gradient that transforms a single air temperature value read by a fixed temperature sensor in the suite of fixed ambient sensors into temperatures at locations across the grow area. For example, upon receipt of a first module-level temperature value from the mover when the mover is occupying a first location over a first module in the grow area at a first time, the system can pair this first module-level temperature value with a first general temperature value recorded by the fixed suite of ambient sensors at approximately the first time. Similarly, upon receipt of a second module-level temperature value from the mover when the mover is occupying a second location over a second module in the grow area at a second time, the system can pair this second module-level temperature value with a second general temperature value recorded by the fixed suite of ambient sensors at approximately the second time. By repeating this process in response to new temperature data recorded by the mover and fixed infrastructure in the facility over time, the system can amass a corpus of concurrent module-level data and generate temperature pairs. From these paired temperature data, the system can train a temperature correction gradient (or map, matrix, etc.) that outputs corrected local temperature estimates at discrete module locations in the grow area given a single temperature value read by the fixed suite of ambient sensors (and given a current time of day and/or time of year).

The system can implement similar methods to develop correction gradients for humidity, air speed, light level, and/or other ambient conditions monitored by the mover and fixed infrastructure in the facility.

The system can therefore leverage local, module-level ambient data recorded by the mover at known locations throughout the grow area while the mover completes module transfer and module scan requests to develop correction gradients that transform single-point ambient data collected by fixed infrastructure in the facility into more accurate ambient conditions at discrete locations occupied by plants throughout the grow area. The system can then transform new general ambient single-point data recorded by fixed infrastructure in the facility into estimates of local ambient conditions at modules throughout the grow area and then write these local ambient condition estimates to corresponding plant records based on module and plant locations stored in module and plant maps described above.

However, the system can implement any other method or technique to leverage module-level data to calibrate general ambient data collected by fixed infrastructure in the facility.

7. Transfer Station and Robotic Manipulator

Figure 3:
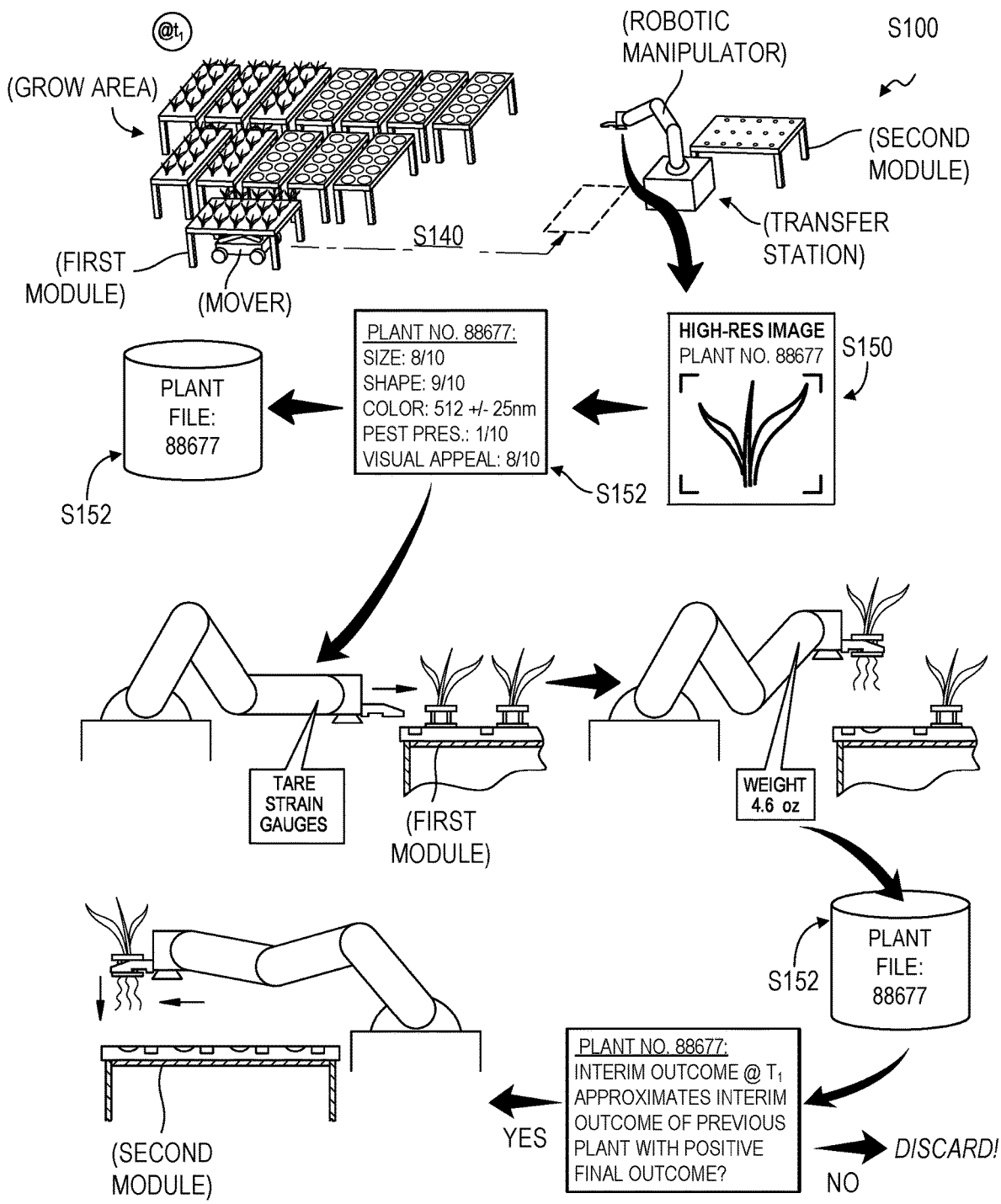
FIG. 3 is a flowchart representation of one variation of the method.

As shown in FIGS. 3 and 5, the system also includes a transfer station arranged within the facility and defining a location at which plants are autonomously inspected and transferred from a first module (e.g., a nursery-type module) containing a higher density of plants slots to a second module (e.g., a finishing module) containing a lower density of plants slots. The system can also include a robotic manipulator: arranged at the transfer station; defining a multi-link robotic manipulator that is sufficiently mobile to reach each plant slot in a module temporarily positioned at the transfer station; including an end effector configured to engage plant cups supporting plants in this module; and/or including an optical sensor (e.g., a multi-spectral camera, or a stereoscopic camera, etc.) configured to record plant-specific images of plants in these modules, as described below.

In particular, the robotic manipulator functions to transfer plants between a first module (e.g., a nursery-type module) exhibiting a first density of plant slots to a second module (e.g., a finishing-type module) exhibiting a second density of plant slots less than the first density. By autonomously moving plants from high-density modules to lower-density modules, the robotic system can ensure that plants have sufficient access to light, water-borne nutrients, and space to continue growing over time. While sequentially transferring single plants between modules, the robotic manipulator can also collect optical and numerical-point data from each, singular plant.

For example, the mover can deliver a nursery-type module to the robotic manipulator at a first time to receive a set of seedlings from a seeding tray; when transferring seedlings into the nursery-type module, the robotic manipulator can record images and weight data for these seedlings. The mover can then return the nursery-type module to its assigned location within the facility. Two weeks later, the mover can return the nursery-type module to the robotic manipulator; the robotic manipulator can then collect images and weight data from these plants while transferring these plants from the nursery-type module to a finishing-type module. The mover can then return the finishing-type module to its assigned location within the facility. Two weeks later, the mover can return the finishing-type module to the robotic manipulator; the robotic manipulator can then collect images and weight data from these plants while transferring these plants from the finishing-type module into boxes for final processing, packaging, and shipment from the facility. The robotic manipulator can therefore collect high-resolution image and weight data from plants at a low frequency (e.g., once per two-week interval); the computer system can then write these high-resolution, low frequency data to plant records assigned to corresponding plants.

7.1 Images

In one implementation, the robotic manipulator includes an articulable optical sensor (e.g., a 2D or 3D color camera or multispectral imager) integrated into or otherwise coupled to the end effector. Upon arrival of a first module at the transfer station, the robotic manipulator can navigate to a position that orients the articulable optical sensor over the first module and then trigger the articulable optical sensor to record a single, 2D photographic image (or "optical scan") of all plants in the first module. Alternatively, upon arrival of the first module, the robotic manipulator can: navigate the articulable optical sensor through multiple preset positions, such as one position over each plant slot in the module; and record a 2D photographic image through the articulable optical sensor at each of these positions. For each of these images, the system can then: query a module map and a plant map of the facility to link an image recorded by the robotic manipulator to a singular plant record; implement methods and techniques described above and below to extract characteristics of a singular plant represented in this image; and store these characteristics (and the image) in the corresponding plant record.

Alternatively, the system can include a 2D or 3D optical sensor (e.g., a 3D scanner) arranged near the robotic manipulator; after removing a plant from the first module, the robotic manipulator can orient the plant proximal the optical sensor, and the optical sensor can record a 2D or 3D scan of the plant before the robotic manipulator places the plant in the second module. For example, the robotic manipulator can orient a plant such that its anteroposterior axis faces the optical sensor at a distance from the optical sensor sufficient to keep the top of the plant's foliage and the bottom of the plant's root structure in the optical sensor's field of view. The optical sensor can thus record an image of the side of this plant. The system can then extract characteristics of both the plant's foliage and the plant's root structure from this image of the side of the plant.

In the foregoing implementation, the robotic manipulator can also manipulate the plant within the field of view of the adjacent optical sensor while the optical sensor records additional 2D or 3D images of multiple faces of the plant; and the system can stitch these 2D or 3D images into a composite, high-resolution 3D image of the entire plant.

However, the robotic manipulator can include or interface with an optical sensor of any other type at the transfer station and can implement any other method or technique to collect optical data of an individual plant when transferring this plant between two modules.

7.2 Weight

In one implementation, shown in FIG. 3, the robotic manipulator includes a set of (e.g., three) strain gauges arranged across three perpendicular axes at a junction between the end effector and an adjacent arm segment (or between the end effector and jaws extending from the end effector). Prior to selecting a first plant from a module nearby, the robotic manipulator can pause its motion, sample the set strain gauges, and store values read from the strain gauges as a tare value in order to calibrate these strain gauges. Once the end effector removes a plant fully from its slot in the module, the robotic manipulator can again sample the set of strain gauges and calculate a weight of the plant based on differences between new strain values read from the strain gauge and stored tare values.

In this implementation, after removing a plant from its slot in the module, the robotic manipulator can read the strain gauges immediately and calculate a weight of a plant accordingly from these data. The system can also multiply this weight value by a wetness coefficient in order to correct the calculated weight of the plant for wetness or dampness of its roots. Additionally or alternatively, once the plant is removed from its slot, the robotic manipulator can: rapidly oscillate the end effector to shake water from the plant's roots into a collection canister below; activate a blower adjacent the plant to blow water from the plant's roots (and away from the module), such as down or laterally into a collection canister); or pause its motion with the plant over a collection canister as water drips from the plant's roots prior to sampling the strain gauges in the robotic manipulator.

However, the robotic manipulator can include any other type of sensor arranged in any other location and configured to output a signal representative of a weight of the plant. The robotic manipulator can also implement any other methods or techniques to calibrate the sensor prior to retrieving the first plant and to interpret a signal read from the sensor as a weight (or mass) of the first plant.

7.3 Image Feature Extraction

Upon receipt of a high-resolution image of an individual plant recorded at the transfer station, the system can extract plant characteristics from the image and write these characteristics to the plant record assigned to this plant.

7.3.1 Plant Size

In one implementation, the system implements computer vision techniques to: detect a boundary of a plant represented in an image; calculate a number of green pixels in the image of a plant (e.g., a number of pixels exceeding a threshold intensity or brightness in the green color channel in the image), which may be indicative of the size of the plant; and/or generate a metric representing a "greenness" of a region of the image corresponding to the plant, which may be indicative of the health of the plant. For example, the system can: implement a color classifier to classify a likelihood that pixels in the image are likely to represent plant matter and then count the number of pixels in the image that are classified as 'likely to represent plant matter'; or implement this process for each color channel in the image, merge classifications for corresponding pixels in each color channel, count a number of pixels in a composite color space that are 'likely to represent plant matter,' and represent the size of the plant based on this pixel count or fill factor—that is, a proportion of foliage or leaf cover area represented in the image. The system can then write these metrics to the plant record assigned to this plant.

7.3.2 Pests

In another implementation, the system can implement computer vision techniques to detect pests affecting a plant shown in an image. For example, the system can scan the image for dark (e.g., black or brown) round or lozenge-shaped spots that may indicate the presence of insects (e.g., ants, aphids, flies, silverfish, moths, or caterpillars, etc.) on the plant. In this example, the system can maintain a counter of such spots (e.g., spots between a minimum and maximum dimension or area) and flag this plant as infected by a pest if the final value of this counter exceeds a threshold value. Furthermore, the robotic manipulator can record a sequence of images of a plant while transferring the plant from one module to the next—or record multiple images of the full length and width of a module—over a period of time (e.g., five seconds), repeat the foregoing methods and techniques to identify such spots in each image in this sequence, implement object tracking techniques to track motion of these spots across these images, confirm that these spots represent insects if these spots are determined to have moved throughout this sequence of images, and then flag the plant as infected by this accordingly. The system can implement similar methods and techniques to detect parasites (e.g., chiggers, ticks, or mites) and/or gastropods (e.g., slugs) on leafy regions of plants shown in the image.

In another example, the system scans the image for dark, discolored leaf regions that may indicate a nematode infestation. In this example, if the system detects any such dark, discolored leaf region in the image of a plant or calculates that a proportion of the leaf area in the plant is so discolored, the system can flag the plant as infected by such a pest. However, the system can implement any other methods or techniques to detect pests directly or to infer the presence of pests in plants in the first module from color data contained in one or a sequence of images of the first module, such as based on images of the first module collected by the fixed infrastructure, the mover, or by the robotic manipulator.

The system can then write features extracted from an image of a plant and suggestive of a pest and/or a pest pressure flag to a plant record assigned to this plant.

7.3.3 Leaf Color and Leaf Area

The system can also extract color values from regions of the image that correspond to leaves or other plant matter and transform these data into a representation of health of the plant shown in the image.

In one implementation, the system implements template matching or object recognition techniques to identify leaves in the image, such as based on template images or models of leaves of plants of the same type and at similar growth stages as the group of plants in the first module. The system can then correlate light-colored (e.g., yellow, tan, brown) regions around perimeters of these leaves with chemical burns or insufficient nutrient supply. The system can also correlate light-colored, low-gloss foliage with heat burns. The system can then write the defect and perceived degree of this defect to the plant record assigned to the plant shown in this image.

The system can also estimate a total leaf area of the plant based on a quantity of green pixels (or a quantity of pixels likely to represent plant matter) in the high-resolution image of the plant. For example, the system can: access a scalar value based on a known offset from the robotic manipulator to the plant slot containing the plant when the high-resolution image of the plant was recorded; and then multiply the quantity of green pixels in the image by this scalar value to estimate a total leaf area of the plant. The system can then calculate a foliage density of the plant based on a ratio of this leaf area to the estimated size of the plant described above, which may correlate to health or viability of the plant.

However, the system can implement any other method or technique to estimate the total leaf area of the plant and/or to characterize health of the plant based on its total leaf area. Furthermore, the system can extract, characterize, and/or label any other singular features or multi-dimensional feature sets from an image of a plant and write these data to a corresponding plant record.

8. Optical Inspection Station

In one variation shown in FIG. 5, the system includes an optical inspection station arranged at the transfer station and physically accessible to the robotic manipulator. In one implementation, the optical inspection station includes: an enclosure defining an aperture configured to receive a plant via the robotic manipulator; a receptacle arranged inside the enclosure and configured to receive and support a plant cup within the enclosure; a set of light elements configured to repeatably illuminate a plant placed over the receptacle by the robotic manipulator; and an optical sensor (e.g., a 2D color camera, a stereoscopic color camera, and/or a multispectral camera, etc.) arranged inside the enclosure over the receptacle and configured to capture a 2D or 3D image of the plant while illuminated by the light elements. In this implementation, the optical inspection station can also include: a rotary table arranged inside the enclosure, supporting the receptacle, and configured to rotate a plant placed in the receptacle while the optical sensor records a sequence of images of the plant.

In the foregoing implementation, upon retrieving a plant from a module temporarily positioned in the module docking location, the robotic manipulator can: deposit the plant onto the receptacle inside the optical inspection station; and then retract the end effector before triggering the optical inspection station to execute a scan routine. During a scan routine, the optical inspection station can: activate the light elements; and trigger the optical sensor(s) to record 2D or 3D images of the plant, such as while the rotary table rotates 360° within the optical inspection station.

Alternatively, the optical inspection station can include an enclosure, a window, a rotary table, and light elements over the rotary table. Upon retrieving a plant from a module temporarily positioned in the module docking location, the robotic manipulator can: place the plant on the rotary table within the optical inspection station; orient the articulable optical sensor on the end of the robotic manipulator to face the plant now located in the optical inspection station; trigger the light elements to activate while the rotary table rotates the plant; and record images of the plant—through the articulable optical sensor arranged on the robotic manipulator—to record images of the plant; and then retrieve the plant from the optical inspection station before depositing the plant into an assigned plant slot in another module.

8.1 Selective Scanning at the Optical Inspection Station

In this variation, the system can scan select plants in the optical inspection station. For example, the robotic manipulator can record one high-resolution plant-level image of each plant in a module—through the articulable optical sensor arranged on the end of the robotic manipulator—for each module delivered to the transfer station by the mover. However, in this example, the robotic manipulator can insert only one plant (or fewer than 10% of plants) per module into the optical inspection station and thus record ultra-high-resolution plant-level images of only one plant (or fewer than 10% of plants) per module delivered to the transfer station. In particular, retrieving a plant from a module, locating the plant in the optical inspection station, recording an ultra-high-resolution plant-level image of this plant, and then retrieving this plant from the optical inspection station may require significantly more time for the robotic manipulator to complete than the robotic manipulator recording an image of the plant with the articulable optical sensor while simultaneously retrieving the plant from the module; the ultra-high-resolution plant-level image of the plant may also require significantly more processing resources to analyze than the high-resolution plant-level image recorded by the articulable optical sensor on the robotic manipulator.

The system can therefore record ultra-high-resolution plant-level images of select plants in order: to limit time spent transferring plants from one module to another, thereby enabling one robotic manipulator to service many (e.g., hundreds, thousands of) modules, each containing many (e.g., 12 or 48) plants; and to limit data storage and data processing load while also enabling the system to access ultra-high-resolution data of select plants that may be representative of many other plants occupying the same module (and even representative of many other plants occupying other modules located nearby in the grow area).

However, the system can implement any other methods or techniques to: select a representative plant from a group of plants in one or more modules; to trigger the transfer station to record a three-dimensional optical scan of the representative plant; and to extract an ultra-high-resolution interim or final outcome of the representative plant from the three-dimensional optical scan.

8.2 Image Feature Extraction

The system can then implement methods and techniques similar to those described above to extract various characteristics of a plant from this ultra-high-resolution image, such as: the size, shape, and color of the plant; pest indicators; indicators of over- and under-exposure to temperature, humidity, light, nutrients, etc.; and/or leaf area or foliage density; etc. In particular, because the image recorded by the optical inspection station (or by the optical inspection station) contains a very high density of optical data of a plant relative to images recorded by the fixed infrastructure, the mover, or by the robotic manipulator when retrieving the plant from a module, the system can extract relatively high-precision, relatively low-error quantitative plant metrics from the ultra-high-resolution image.

As described above, the system can store these high-precision, low-error quantitative plant metrics in a plant record assigned to the corresponding plant.

9. Lab Testing and Consumer Feedback

In one variation shown in FIG. 1, physical whole or partial plant samples are collected from plants and lab tested: to determine composition (e.g., nutrient composition) of these plants; to identify pests or disease vectors in these plants; and/or to qualify flavor profile or aroma of these plants. In particular, the system can flag a small subset of plants for lab testing, such as one plant in one thousand viable plants harvested in the facility. The system can thus trigger selective collection of plant metrics in additional dimensions—such as composition, pathogen vector, aroma, and/or flavor—from a relatively small proportion of plants grown in the facility.

In one example, a human operator manually collects (e.g., cuts) physical samples from plants flagged by the system, labels these samples, and packages these samples for lab testing. Alternatively, the robotic manipulator can automatically collect physical plant samples from select plants over time, such as responsive to plant sample requests issued by the computer system. For example, the robotic manipulator can include an exchangeable cutting end effector including a blade or scissor configured to cut samples from plants. When the system flags a plant for lab testing (e.g., every $1,000^{th}$ plant) and a module containing this plant is delivered to the robotic manipulator, the robotic manipulator can: autonomously engage the cutting end effector; cut a sample from the flagged plant; dispense this sample into a labeled lab test package; retrieve the standard end effector for transferring plants between modules; and resume transferring plants out of this module and into an adjacent module. Alternatively, the robotic manipulator can remove an entire plant from a module and place this plant in a separate labeled lab test package. These whole or partial plant samples can then be delivered to a test facility, such as an external lab, for testing.

Upon receipt of lab results for a sample—such as including composition, pest or disease vector, aroma, and/or flavor profile of this sample—the system can write these lab results to the plant record associated with this plant.

The system can additionally or alternatively flag a particular plant for additional human labeling. For example, the system can prompt a human to indicate visual appeal of a particular plant through a grower portal executing on a computing device. In this example, the system can prompt the human to provide this feedback for a particular plant while overseeing automated transfer of many plants out of a module at the transfer station. Alternatively, the system can serve a prompt to provide an indicator of visual appeal (e.g., on a scale from "0" to "10" or on a scale from "unsalable" to "very saleable") for a particular plant through the operator portal and include a location of the module and the address of the plant slot in this module that is currently occupied by the particular plant. The system can then write the human's feedback response to this prompt to the plant record associated with this plant.

The system can also prompt a human to indicate ideal size, shape, aroma, flavor profile, and/or nutrient composition. For example, upon receipt of aroma, flavor profile, and/or nutrient composition test results for a particular plant from an external lab, the system can prompt a human operator in the facility to indicate proximity of the aroma, flavor profile, and/or nutrient composition to target values; and the system can store this feedback in a plant record associated with the particular plant.

However, the system can collect any other human feedback and/or external test data for select plants grown within the facility.

10. Aggregating Plant Data

Therefore, the system can: extract low-resolution optical information (e.g., plant size, plant color) for each plant in the facility from images recorded by the fixed optical sensor at a relatively high frequency (e.g., once per ten-minute interval) as these plants grow over time (e.g., over an eight-week growth cycle); extract moderate-resolution optical information for each plant in the facility from images recorded by the mover at a moderate frequency (e.g., once per day) as the mover interfaces with individual modules within the facility according to module transfer and/or module scan requests; and extract relatively high-resolution optical information for each plant in the facility from images recorded at the transfer station at a relatively low frequency (e.g., once per two-week interval) as the robotic manipulator moves individual plants into and out of modules. The system can store these plant characteristics—such as plant size (e.g., height, width), color, leaf area, and/or foliage density—derived from low-, moderate-, and high-resolution images recorded during growth of an individual plant as interim outcomes of this plant in the plant's assigned file. For example, the system can store each interim outcome of a plant with a timestamp based on a time since the plant was first planted in a seeding tray or first loaded into a nursery-type module (hereinafter a "reference date"). In this example, the system can also weight or prioritize these interim outcomes based on the quality (e.g., the resolution) of the image from which these interim outcomes were derived, such as by assigning a lowest weight to interim outcomes extracted from low-resolution images collected by the fixed infrastructure and a greatest weight to interim outcomes extracted from optical data collected by the optical inspection station.

The system can similarly store plant characteristics derived from a high-resolution image and/or an ultra-high-resolution image—recorded at the transfer station when a plant is harvested—as a final outcome of this plant in the plant's assigned file.

The system can also store indicators of pest pressures—derived from these low-, moderate-, and/or high-resolution images—as growth input parameters for these plants represented in these images. For example, because presence of pests may affect growth of a plant and the plant's final outcome, such as by reducing access to nutrients or by consuming plant matter, the system can store a probability of pest presence, a type of pest present, and/or a magnitude of pest infestation for an individual pest—derived from low-, moderate-, and/or high-resolution images of this plant—as growth input parameters in the plant's assigned file. The system can also timestamp these pest-related growth input parameters based on times that these images were recorded, as described above.

Similarly, the system can store ambient condition and water quality data collected by the fixed infrastructure and the mover during growth of plants in the facility as growth input parameters for these plants. For example, the system can write ambient condition and water quality growth input parameters to a plant record associated within a particular plant, including a timestamp representing a time that these data were collected after a reference time of the particular plant and including a weight or priority of these data (e.g., a low weight if recorded by fixed infrastructure and higher weight if recorded by the mover).

10.1 Data Structure

Therefore, as optical and numerical-point data uniquely representing many (e.g., thousands, millions) of plants within the facility are collected over time, the system can fuse these data into unique multi-dimensional temporal representations of these plants, including: inputs that affect growth of a plant; states of the plant at distinct intervals throughout its growth cycle (or "interim outcomes"); and a final outcome of the plant, such as its health, visual appeal (e.g., color and size), flavor profile, and nutrient composition upon the conclusion of the growth cycle.

In one implementation, the system handles various time-stamped numerical-point data collected over a plant's growth cycle as input parameters affecting growth of the plant, such as including: plant cultivar (or "strain") identifier; ambient light level; supplemental light level; total light level; air speed; relative humidity; ambient temperature; water temperature; water pH; dissolved nutrient (e.g., oxygen, nitrogen) levels; etc.

In a similar example, the system can calculate: average air temperatures proximal the plant over discrete time intervals of one hour over an eight-week growth cycle after the plants reference time; average ambient humilities proximal the plant over discrete time intervals of four hours over the eight-week growth cycle; variance of dissolved oxygen in the module occupied by the plant over discrete time intervals of one day over the eight-week growth cycle; variance of pH in the module occupied by the plant over discrete time intervals of twelve hours over the eight-week growth cycle; and variance of nutrient level in the module occupied by the plant over discrete time intervals of two days over the eight-week growth cycle; etc. The system can write these values to corresponding predefined element positions in the plant's vector to form a dense quantitative representation of the plants exposure to various input parameters over the plant's eight-week growth cycle. In this example, the system can similarly represent interim outcomes of the plant in absolute or relative quantitative values on daily intervals in the plant's vector.

The system can further represent presence, type, and/or magnitude of pest pressure detected at a plant as quantitative values and write these values as input parameters in the plant vector. As additional numerical-point data are collected over time for the plant and stored in a plant record assigned to this plant, the system can aggregate these data into a multi-dimensional vector representing these input parameters over the plant's growth cycle.

The system can also label the multi-dimensional vector representing the plant with plant outcomes. For example, the system can: extract a final foliage size, final foliage shape (or "fullness"), final root size, a number of leaves, and final foliage color of a plant from a final image of the plant recorded by the robotic manipulator prior to processing, packaging, and shipment of the plant from the facility; and then label the corresponding vector with these outcomes. When available for the plant, the system can also retrieve flavor profile test data, lab result (e.g., nutrient) data, final weight, and either acceptance or rejection of the plant by a buyer and label the vector with these data. The system can thus construct a single multi-dimensional vector representing multiple input parameters and labeled with multiple outcomes for one plant grown in the facility. In particular, the vector: can contain quantitative metrics of the plant's exposure to multiple inputs over time during its growth; can be labeled with the plant's outcome; and can thus represent a link between input parameters, interim outcomes, and a final outcome for this unique plant.

(Alternatively, the system can fuse select outcomes into a quantitative or qualitative measure of the success of the plant. For example, the system can calculate a linear combination of the outcomes according to preset weights, wherein the value of the linear combination is directly proportional to the plant's final size, proximity to a target color, proximity to a target shape, proximity to a target nutrient level, and salability and is inversely proportional to a final size of the plant's roots (which, when large, may impede transfer between modules and represent waste), the plant's growth rate (e.g., overall size per unit time of its growth cycle), and time from packaging to sale of the plant. The system can then label the vector with this singular metric of "plant success.")

The system can also associate the vector with quantitative representations of interim outcomes of the plant, such as extracted from low-, moderate, and high-resolution images and/or from operator feedback recorded throughout the plant's growth cycle. As described below, these features can later be compared to features of a new plant—similarly extracted from images of the new plant recorded during its growth cycle—to determine the growth trajectory of the new plant, to predict the new plant's final outcome (e.g., final size, final weight, final color, final flavor profile, and/or salability, etc.); and to inform adjustment of input parameters for the new plant in order to align its growth trajectory to that of a previous plant with a known positive final outcome.

The system can implement the foregoing processes for each plant grown in the facility in order to generate a (large) set of unique multi-dimensional vectors representing unique plants and labeled with final outcomes of these unique plants.

However, the system can implement any other methods or techniques to package data—including input parameter data and outcomes derived from data collected over the growth cycle of a plant—into a data container. The system can then compare this data container to data containers representing other plants grown in the facility to isolate links between input parameters and outcomes of plants grown in the facility and to refine a grow schedule for these plants accordingly.

11. Correlation: Input Parameters and Final Outcomes

Once the system has generated this set of multi-dimensional vectors representing various input parameters and known outcomes of plants grown in the facility, the system can derive correlations between ranges of input parameters and various outcomes.

In one implementation shown in FIG. 2, the system implements structured data analysis (e.g., linear regression analysis), cluster analysis, and/or other statistical analysis and machine learning techniques to quantify correlation between various input parameters and: plant size; plant weight; plant shape; plant color; flavor profile; nutrient composition; and/or visual appeal; etc. for plants grown in the facility. For example, the system can identify temporal ranges of input parameters—over the course of the growth cycle of a plant—that exhibit strong correlation to: at least a minimum plant size; at least a minimum plant weight; a plant shape within a target shape window; a plant color within a target color range; a flavor profile within a profile range; and/or a nutrient composition within a target composition range at the conclusion of the growth cycle.

11.1 Weighted Outcomes

In this implementation, the system can also assign greater weights or priorities to select final outcomes. For example, the system can: assign a first weight to a target color range, since color may be a greatest initial attractant to produce for a customer; assign a second weight less than the first weight to a target size range, since larger produce units may be more attractive to consumers but may be more difficult to package up to a threshold size; assign a third weight less than the second weight to flavor profile, since flavor—which may be informed by nutrient composition—may affect repeat purchases by consumers and since flavor consistency may be valued by consumers; and assign a fourth weight less than the third weight to smaller root structures, since smaller root structures ease transfer of plants between modules, ease module cleaning, and reduce plant waste.

11.2 Regression Techniques

The system can implement linear regression techniques to quantify strengths of relationships between various input parameters to which a plant is exposed over time (e.g., an eight-week growth cycle) and the outcome of the plant based on similarities and differences of time series input parameters and outcomes stored in these many (e.g., thousands, millions of) multi-dimensional vectors representing plants grown in the facility over time.

In one implementation, the system can identify ranges of input parameters—occurring over time—that yield a suitable compromise of these weighted outcomes. For example, the system can: identify a group of vectors associated with a group of plants exhibiting near-optimum compromises of the weighted outcomes or representing near-maximization of the weighted outcomes; identify a first set of input parameters—represented by vectors in this first set—that exhibit strong similarities (e.g., narrow distribution of values) and define nominal target values and tight tolerances for input parameters in this first set accordingly; identify a second set of input parameters—represented by vectors in this second set—that exhibit moderate similarities (e.g., moderate distribution of values) and define nominal target values and moderate tolerances for input parameters in this second set accordingly; and identify a third set of input parameters—represented by vectors in this third set—that exhibit wide differences (e.g., large distribution of values) and define nominal target values and loose tolerances for input parameters in this third set accordingly. The system can implement similar methods for each input parameter independently and then calculate nominal target values (e.g., based on time from plant seeding) and define tolerances proportional to distribution of the input parameter across the set of vectors for "ideal" plants in order to generate a grow schedule that specifies target or target ranges of: natural light; supplemental light; total light; air speed; relative humidity; ambient temperature; water temperature; water pH; dissolved nutrient (e.g., oxygen, nitrogen) levels; etc. over time in order to achieve "ideal" plants.

In another implementation, the system implements clustering techniques (e.g., k-means clustering techniques) to group subsets of many (e.g., thousands, millions of) multi-dimensional vectors—representing plants harvested at the facility over time—by similarity of known final outcomes (e.g., weight, diameter, height, color, pest presence). For a cluster of vectors representing plants with like outcomes, the system can then derive strengths of relationships between input parameter values (e.g., time series of discrete input parameters values, input parameters ranges, or input parameter variance) stored in these vectors and a final plant outcome represented by this cluster based on similarities and differences between input parameter values stored in these vectors. The system can repeat this process for each other cluster of vectors. By comparing derived relationships between input parameters and final plant outcomes across multiple clusters representing plants of different final outcomes (e.g., different sizes, geometries, colors, flavor profiles, etc.), the system can further refine these derived relationships.

Alternatively, the system can implement clustering techniques to group subsets of many multi-dimensional vectors—representing plants harvested at the facility over time—by similarity of input parameter values contained in these vectors. The system can label these clusters with plant outcomes, such as: human-supplied visual appeal, flavor profile, and/or composition feedback; human-supplied indication of proximity to target visual appeal, flavor profile, and/or composition; and/or size, shape, color, weight, and/or geometry outcomes extracted from data collected at the transfer station when these plants were harvested. The system can then implement regression techniques to derive strengths of relationships between input parameter values and these final outcomes based on similarities of input parameter data stored in vectors in one cluster and differences in input parameter data stored in vectors in this cluster and stored in vectors in other clusters. The system can additionally or alternatively calculate variance in final outcomes based on differences in final outcomes associated with clusters of vectors representing very similar input parameters through the growth cycles of corresponding plants grown in the facility.

The system can therefore derive strengths of relationships between: each of [plant cultivar, ambient light level, supplemental light level, total light level, air speed, relative humidity, ambient temperature, water temperature, water pH, and/or dissolved nutrient level, etc.] each second, minute, hour, day, or week over a growth cycle of a plant; and each of the [size, shape, weight, geometry, color, flavor, aroma, composition, and/or pest presence, etc.] of the plant at the conclusion of the growth cycle. The system can store these relationships between input parameters and final outcomes in a plant model for plants grown in the facility, as shown in FIG. 2.

11.3 Default Grow Schedule

Based on this plant model, the system can isolate time series of discrete input parameter values, input parameters ranges, and/or input parameter variances for various input parameters over a growth cycle of a plant that are likely to yield: "ideal" plants; "sufficient" plants; and "rejected" plants. The system can then construct a default grow schedule that defines: a time series of target input parameter values and permissible ranges (or variances, tolerances) for these input parameters; and a schedule for planting seeds, transferring seedlings into nursery modules, transferring plants from nursery-type modules into finishing modules, and harvesting plants from finishing-type modules that, when implemented over a growth cycle of a plant, is predicted to yield an "ideal" plant (or at least a "sufficient" plant of suitable size, weight, geometry, color, and/or flavor profile, etc. and not a "rejected" plant).

The system can implement closed-loop controls: to autonomously drive ambient humidity, ambient temperature, ambient light level, and wind speed over each module and to drive water temperature, water pH, and nutrient level within each module toward this default grow schedule based on low-, moderate-, and high-resolution ambient, local, and plant-specific data collected by infrastructure in the facility over time; and to autonomously trigger the module and transfer station to cooperate to transfer and harvest plants from modules in order to grow many "ideal" plants with limited human input or oversight.

However, the system can implement any other methods or techniques to transform labeled multi-dimensional vectors—representing plants grown in the facility—into a grow schedule defining input parameter ranges for growing "ideal" plants in the facility.

11.4 Additional Relationships and Modified Grow Schedules

The system can implement similar methods and techniques to derive strengths of relationships between: each of [plant cultivar, ambient light level, supplemental light level, total light level, air speed, relative humidity, ambient temperature, water temperature, water pH, and/or dissolved nutrient level, etc.] each second, minute, hour, day, or week over a growth cycle of a plant; and each of the [size, shape, weight, geometry, color, composition, and/or pest presence, etc.] of the plant at certain instances within the plant's growth cycle—such as daily or bi-weekly—based on interim outcomes extracted from low-, moderate-, and high-resolution images of the plant. In particular, the system can implement clustering, regression, and/or other methods and techniques described above to derive strengths of relationships between: interim outcomes of a plant in various dimensions (e.g., size, shape, weight, geometry, color, and/or pest presence) at certain times in the growth cycle of the plant; and various input parameters to which the plant is exposed from the reference date of the plant up to these times in the growth cycle of the plant.

The system can also implement similar methods and techniques to derive strengths of relationships between interim outcomes of plants and final outcomes of plants. In particular, the system can: identify interim outcomes in certain dimensions (e.g., sizes below a threshold size, colors outside of a target color range, or pest infestation above a threshold degree of pest infestation) that are strong indicators of poor final outcomes (e.g., poor visual appeal, underweight outcome, undersize outcome, poor flavor profile, poor aroma); and identify other interim outcomes in certain dimensions that are strong indicators of positive final outcomes. The system can then autonomously shift resources from a first group of plants exhibiting interim outcomes indicating poor final outcomes to a second group of plants exhibiting interim outcomes indicating positive final outcomes. For example, the system can isolate certain interim outcomes for young (e.g., two-week-old) plants that exhibit strong correlation to poor final outcomes (e.g., underweight, poor visual appeal, pest presence). Upon receipt of a global, module-level, or plant-specific image of a new plant, the system can extract an interim outcome of this new plant from the image. If this interim outcome of the new plant sufficiently approximates an interim outcome previously associated with a poor final outcome in one or more dimension, the system can flag the new plant to be culled from the grow area in order to reduce resource load (e.g., light, nutrients, air quality control) that may otherwise have been allocated to grow this plant to a poor final outcome. The system can then dispatch the mover to deliver a module containing this new plant to the transfer station—such as immediately or according to a next scheduled transfer for this module—and prompt the robotic manipulator to remove the new plant from its module and to discard the new plant into a compost bin.

In another example, the system can identify an interim outcome that exhibits weak correlation to either positive or poor outcomes. Given such understanding of weak correlation between this interim outcome and a final outcome, the system can then identify plants exhibiting such interim outcomes and reallocate resources to these plants (e.g., more frequent monitoring with the mover and transfer station, more frequent water and nutrient replenishing, relocation to a grow area with tighter ambient controls, etc.) in order to drive these plants toward positive outcomes.

In yet another example, the system can identify an interim outcome that exhibits strong correlation to positive final outcomes. Given such understanding of strong correlation between this interim outcome and a final outcome, the system can then identify plants exhibiting similar interim outcomes and reallocate resources away from these plants (e.g., less frequent monitoring, less frequent water and nutrient replenishing, relocation to a grow area with looser ambient controls, etc.) in order to minimize resource load in the facility without substantive decrement in final plant outcomes.

The system can therefore leverage interim plant outcomes derived from low-, moderate-, and high resolution data collected within the facility over high-, moderate-, and low-frequencies to inform intelligent allocation of resources to plants that may be influenced toward positive outcomes and intelligent early culling of plants unlikely to achieve positive outcomes.

Furthermore, the system can: implement methods and techniques described above to characterize relationships between: input parameters for plants grown in the facility up to a particular instance in the growth cycle of these plants; and interim outcomes of these plants at this instance in the growth cycle. From these relationships, the system can generate a modified grow schedule from a particular interim outcome within a growth cycle to a particular positive final outcome; upon detecting a new plant at this particular interim outcome, the system can then autonomously implement this modified grow schedule proximal this new plant in order to drive this new plant toward this positive final outcome.

The system can similarly generate a modified grow schedule from a first interim outcome at a first time within a growth cycle (e.g., exhibiting weak correlation to a positive outcome) to a second interim outcome at a later time within the growth cycle (e.g., exhibiting stronger correlation to a positive outcome); upon detecting a new plant at the first interim outcome at approximately the first instance within its growth cycle, the system can then implement this modified grow schedule proximal a module containing this new plant (e.g., by moving the module to a location in the grow area exhibiting ambient conditions better approximating conditions specified in this modified grow schedule, by modifying a dosing schedule for reconditioning water in the module) in order to drive this new plant toward the second interim outcome.

The system can implement the foregoing methods and techniques: to re-characterize relationships between input parameters and interim and final outcomes based on new data recorded by infrastructure in the facility over time; and to revise the default and modified grow schedules based on these revised relationships between input parameters and outcomes.

12. Testing Grow Schedules

Once the system thus generates a new (default or modified) grow schedule, the system can test the grow schedule on a relatively small batch of plants. For example, over the course of a growth cycle of fixed duration (e.g., eight weeks), the system can implement closed-loop controls to automatically manipulate actuators within the facility to achieve target ranges of input parameters defined by the new grow schedule for a test module containing a test batch of new plants based on ambient, water quality, and plant-specific data collected by fixed and mobile infrastructure within the facility. In this example, the system can: automatically adjust brightness and/or times of day that supplemental lighting is active over a separate test grow area occupied by the test module; adjust speed and/or times of day that fans near the test module are active; adjust a humidity level setting of humidifier/dehumidifier near the test module; adjust a temperate setting of an HVAC system or a flow setting at an HVAC vent near the test module; adjust water nutrient targets and a nutrient refill schedule for the test module; etc. over the course of the growth cycle for this batch of test plants.

In this foregoing example, throughout the growth cycle of these test plants, the system can implement methods and techniques described above to: collect images of plants in this test module; extract interim and final outcomes of these test plants from these images; and construct new vectors representing input parameters of these test plants throughout their growth cycles and their interim and final outcomes. The system can then: automatically qualify the test plants as exhibiting positive or poor interim and final outcomes based on proximity of these vectors to clusters associated with certain positive and poor outcomes; and/or prompt a human operator to label final outcomes of these plants as positive or poor, as described above. The system can then confirm whether the modified grow schedule yielded an expected outcome for the test plants based on: differences between the modified grow schedule and actual exposure to input parameters for these test plants; and derived correlations between input parameter time series and plant outcomes described above.

The system can thus calculate a modified grow schedule based on historical input parameters and outcome data for plants grown at the facility and test this modified grow schedule within a small set of test plants to confirm that this modified grow schedule achieves expected results before expanding this modified grow schedule throughout the entire facility. In particular, the system can: generate a new grow schedule defining target ambient conditions for a new plant over a growth cycle of the new plant and predicted to yield a positive final outcome for the new plant based on derived strengths of relationships between ambient conditions and final outcomes of plants grown in the facility; autonomously adjust actuators within the facility based on ambient and water quality data recorded by fixed and mobile sensors in the facility in order to realize the new grow schedule proximal a module loaded with a new set of plants over a period of time; calculate a predicted final outcome of the new set of plants based on ambient and water quality data recorded by the suite of fixed sensors during this period of time and derived relationships between ambient conditions and water quality and final outcomes of plants grown in the facility; and then assign this new grow schedule to other modules throughout the facility if final outcomes of these new plants align with the predicted positive final outcome.

12.1 Select Input Parameter Testing and Select Outcome Metric Acquisition

The system can implement similar methods and techniques to: select a particular input parameter for which a relationship with a particular outcome metric is unknown or poorly supported; generate multiple modified grow schedules with different magnitudes, tolerances, and/or temporal variances of this particular input parameter; autonomously implement these modified grow schedules across small sets of test plants; collect interim and final outcome metrics for these test plants; prompt a human operator to provide feedback regarding the particular outcome metric for select plants in these test batches; and then implement regression techniques to recalculate the strength of the relationship between the particular input parameter and the particular outcome metric based on ambient, water, and plant-specific data collected throughout the growth cycles of these test plants.

In this implementation, the system can also selectively trigger the transfer station to record ultra-high-resolution images of select test plants from this batch and/or selectively trigger tests plants from this batch for external composition, flavor, aroma, pest, and/or other tests in order to enable the system to access more complete descriptions of the final outcomes of these test plants.

In another implementation, in response to a final (or interim) outcome of plants (e.g., colors, sizes, and/or geometries of these plants) in a module differing from final (or interim) outcomes of a corpus of plants grown previously in the facility—as represented in the corpus of plant records—the system can: select a representative plant in this module; and prompt a human operator to indicate visual appeal of the representative plant in this module.

The system can update corresponding plant records with these new, selective data and recalculate relationships between input parameters, interim outcomes, and/or final outcomes, as described above. The system can then refine a default growth schedule and/or modified grow schedules for all or select plants in the facility—such as by modifying the target magnitude, tolerance limits, and/or temporal variance of this particular input parameter throughout a plant's growth cycle—based on this relationship between the particular input parameter and the particular outcome metric.

12.2 Input Parameter Tolerances

The system can implement similar methods and techniques to test looser tolerances for a particular input parameter, which may reduce resource load for monitoring and maintaining plants growing in the facility. For example, the system can implement the foregoing methods and techniques to define and implement a test grow schedule specifying loosened tolerances for water nutrient levels for a batch of test plants, which may require the mover to execute water quality tests at a test module occupied by the test plants at a reduced frequency, require the mover and/or the transfer station to replenish water and nutrients in the test module at lower frequency, and thus enable the mover and the transfer station to service more modules in a given period of time. The system can then: confirm whether greater variance in water quality in this test module over time yielded no or minimal decrease in final outcomes of these test plants based on images recorded by infrastructure in the facility and/or supplied by a human operator; and update the default grow schedule for plants across the facility to reflect these loosened tolerances on water nutrient level accordingly.

Therefore, the system can isolate input parameters that exhibited weakest relationships to positive outcomes in these plants and relax tolerances or constraints on these input parameters in order to reduce production costs. The system can also: isolate other input parameters that exhibited strongest relationships to positive outcomes; tighten tolerances and constraints on these input parameters in order to better ensure positive outcomes in the future; and adjust sensing schedules for infrastructure in the facility to collect data for these input parameters at greater frequency in order to enable the system to rapidly respond to deviations from target values or from target ranges for these input parameters, thereby enabling the system to better ensure positive outcomes for all plants grown in the facility. The system can thus refine the default grow schedule for future plants to reflect these tested and verified target magnitudes, tolerance limits, and/or temporal variances for these input parameters accordingly.

However, the system can implement any other methods or techniques: to fuse input parameter data collected through various infrastructure in the facility and interim and final outcomes extracted from optical data, external test data, and human operator-supplied feedback for plants grown in the facility over time to calculate relationships between these input parameters and final outcomes; to recalculate a grow schedule accordingly; to test the new grow schedule; to propagate positive grow schedule changes throughout the facility; and to repeat this process over time in order to maintain and increase yield of high-quality plants while reducing time and/or cost to produce each plant.

13. Local Closed-Loop Controls

The system can also track new plants during their growth cycles and implement closed-loop controls to adjust grow schedules for these new plants based on differences and similarities between interim outcomes of these new plants and interim outcomes of previous plants of known final outcomes. For example, the system can: retrieve a first image of a new plant at a particular stage of development (e.g., at a particular time after seeding); access a set of template images of previous plants at or near this same stage of development and of known final outcomes; and then implement computer vision techniques to match the first image to a nearest second image in the set of template images. If the known outcome of the second plant is positive (e.g., near an "ideal" plant), the system can continue to implement the existing grow schedule for the new plant. However, if the known outcome of the second plant is negative or far from an "ideal" final outcome, the system can: access a subset of template images to include only images of previous plants at or near this same stage of development and of known positive final outcomes; implement computer vision techniques to match the first image to a nearest third image in this subset of template images; and define a custom grow schedule for the new plant based on the third plant's input parameter exposure after this stage of development. The system can then autonomously implement the custom grow schedule at or around the first plant in order to drive the first plant toward the known positive outcome of the third plant.

In another example, the system can: access a module-level image of a new module—containing a set of new plants and occupying the grow area—recorded by the mover at a particular time in the growth cycle of the set of new plants; and extract an interim outcome of a particular plant occupying the new module (e.g., a size, color, and or indicator of pest presence) from this module-level image. The system can then scan a corpus of plant records of previous plants to identify a previous plant that exhibited a previous interim outcome—at this same stage of development—nearest the interim outcome of the particular plant (e.g., based on similarities in interim outcomes at the same time since reference dates for the particular and previous plants, as stored in corresponding plant records). If a final outcome of the previous plant differs from a target final outcome for plants grown in the facility (e.g., if the final outcome of the previous plant indicates a size different from a target plant size, a color differing from a target plant color, and/or a degree of pest presence exceeding a threshold pest presence), the system can flag the particular plant for culling from the new module, such as immediately (e.g., prior to a scheduled completion of the growth cycle of the particular plant) or during a next scheduled delivery of the new module to the transfer station. Thus upon delivery of this new module to the transfer station, the robotic manipulator can: optically scan the new module; detect the particular plant in the new module; navigate an end effector to the particular plant; remove the particular plant from the new module; and discard the particular plant, such as into a compost bin.

Alternatively, in the foregoing implementation, if the previous plant—matched to the particular plant at this particular development stage—is associated with a final outcome that sufficiently approximates a target final outcome, the system can: extract ambient and water quality conditions proximal the previous plant—from the particular stage of development to harvest—stored in a plant record associated with the previous plant; shift target ambient and water quality conditions for the new module into alignment with the ambient and water quality conditions experienced by the previous plant after this development stage; and implement closed-loop controls to realize these modified target ambient and water quality conditions in and around the new module, thereby increasing likelihood that plants in the new module achieve positive final outcomes.

The system can implement similar methods and techniques for an entire group of plants in a module, across a group of modules arranged within a particular region of the grow area in the facility, or across the facility in its entirety. For example, if the system determines—from low-, moderate, or high-resolution images of the grow area, individual modules, or individual plants—that plants within a module are generally undersized for their current stage of development (e.g., are expressing interim outcomes best matched to interim outcomes of previous plants that were undersized at a scheduled harvest time), the system can modify a grow schedule for this module to increase input parameters that exhibit strong positive correlation to increased plant size (i.e., based on derived relationships between input parameters and interim and final outcomes described above). In this example, the system can then: dispatch the mover to shift the module into a module location in the grow area that receives a higher incidence of light (e.g., based on a light level map developed by the mover while navigating throughout the grow area); and/or update a nutrient dose schedule for the module to receive more nutrients and dispatch the mover to deliver the module to a dosing station in the facility for adjustment of its water quality. In another example, if the system determines—from low-, moderate, or high-resolution images of the grow area, individual modules, or individual plants—that plants within a module are too light in color, the system can modify a grow schedule for this module to decrease input parameters that exhibit strong positive correlation to increased "yellowness" in plant foliage. In this example, the system can then: dispatch the mover to shift the module into a location in the grow area that receives a lower incidence of light; and/or update a nutrient dose schedule for the module to slightly increase the pH of water and dispatch the mover to deliver the module to the dosing station for adjustment of its water quality.

However, the system can implement any other methods or techniques to adjust a grow schedule for a single plant or group of plants based on differences between optical data of these plants and optical data of previous plants—of known outcomes—at similar stages.

14. Humidity Control

In one variation, the system can: access a series of global and/or local humidity data recorded by fixed and module sensors in the facility over a period of time; derive relationships between ambient humidity and final outcomes of plants grown in the facility; and set a target humidity range in the grow area—predicted to yield positive final outcomes or otherwise not yield poor final outcomes—based on derived relationships between ambient humidity and final outcomes of plants grown in the facility. In particular, by collecting low-resolution global humidity conditions at a high frequency (e.g., once per minute) through the suite of fixed sensors and higher-resolution local humidity conditions proximal known modules at a lower frequency through a humidity sensor in the mover as ambient conditions in the facility change and as many batches of plants are grown and harvested in the facility over time, the system can compile a dense corpus of humidity conditions experienced by plants throughout their growth cycles. Given known final outcomes of these plants, the system can derive a relationship between humidity conditions over various periods within the growth cycle of a plant and the final outcome of this plant.

Furthermore, humidity within the grow area may be a function of total leaf area of plants occupying the grow area and may be represented in a predefined plant transpiration model or in a plant transpiration model developed (or "learned") by the system over time. Therefore, the system can: estimate leaf areas of plants occupying modules in the grow area based on features extracted from global, module-level, and/or plant-specific images recently recorded by sensors in the facility; and predict a humidity in the grow area at a future time based on a sum of leaf areas of plants occupying the grow area and the plant transpiration model. The system can then take preemptive action to control humidity in the grow area if the predicted humidity in the grow area at the future time exceeds the target humidity range set by the system.

For example, to preemptively reduce humidity in the grow area, the system can: scan global, module-level, and/or plant-specific images recently recorded by sensors in the facility for a group of plants—occupying a particular module currently located in the grow area—exhibiting characteristics nearest a target outcome (i.e., a particular module containing a group of plants most ready for harvest); dispatch the mover to autonomously deliver the particular module to the transfer station; and then trigger the transfer station to harvest the group of plants from the particular module. Therefore, though the particular group of plants may not have reached the conclusion of its growth cycle, the system can automatically elect to harvest these plants early—given that the plans sufficiently approximate a target final outcome—in order to reduce total leaf area in the grow area, thereby reducing total transpiration in the grow area, and thus reducing humidity in the grow area in the future without increasing power consumption by a dehumidifier or other HVAC controls in the facility.

In another example, the system can: scan global, module-level, and/or plant-specific images recently recorded by sensors in the facility for a group of plants—occupying a particular module currently located in the grow area—exhibiting interim outcomes that exhibit poor correlation with a target outcome (i.e., a particular module containing a group of plants least likely to reach a positive final outcome); dispatch the mover to autonomously deliver the particular module to the transfer station; and then trigger the transfer station to cull (i.e., dispose of) the group of plants from the particular module. Therefore, the system can selectively cull plants least likely to achieve positive final outcomes in order to reduce total leaf area in the grow area, reduce total transpiration in the grow area, and preemptively reduce future humidity in the grow area.

The system can implement similar methods and techniques to preemptively harvest and/or cull select plants occupying the grow area in order to maintain future temperatures in the grow area—which may also be a function of leaf area and plant transpiration—within a target temperature range that the system has correlated with positive final plant outcomes (or a target temperature range that the system has not correlated with poor final outcomes).

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for monitoring growth of plants within a facility comprising:
    accessing a series of ambient conditions captured by a fixed sensor unit arranged proximal a grow area within the facility, wherein the conditions are captured at a first frequency during a first time period;
    writing the series of ambient conditions to a corpus of plant records associated with plants occupying a group of modules within the grow area based on known locations of modules within the grow area, the corpus of plant records comprising a first set of plant records associated with a first set of plants occupying a first module, in the group of modules, during the first time period;
    dispatching a mover to autonomously deliver the first module from the grow area to a transfer station;
    for each plant in the first set of plants:
        interpreting a final outcome of the plant based on plant-level data captured by the transfer station while transferring the plant out of the first module during a second time period succeeding the first time period; and
        writing the final outcome of the plant to a plant record, in the first set of plant records, associated with the plant; and
    deriving relationships between ambient conditions and final outcomes of plants within the facility based on the corpus of plant records associated with plants grown in the facility.

2. The method of claim 1:
    wherein aggregating global data captured by the fixed sensor unit during the first time period comprises aggregating ambient conditions measured by the fixed sensor unit at the first frequency during the first time period;
    wherein deriving relationships between ambient conditions and final outcomes based on the corpus of plant records comprises deriving strengths of relationships between ambient conditions, measured at the first frequency, and outcomes of plants grown in the facility; and
    further comprising:
        generating a new grow schedule defining target ambient conditions for a new plant over a growth cycle and predicted to yield a target final outcome for the new plant based on strengths of relationships between ambient conditions and final outcomes of plants grown in the facility; and
        for a second module loaded with a second set of plants and occupying the grow area during a third time period succeeding the second time period, autonomously adjusting actuators within the facility according to the new grow schedule based on ambient conditions measured by the fixed sensor unit during the third time period.

3. The method of claim 1, wherein interpreting the final outcome of the plant for each plant in the first set of plants further comprises, for each plant in the first set of plants:
    accessing a plant-level image of the plant captured by the transfer station while transferring the plant out of the first module during the second time period;
    extracting a set of features from the plant-level image of the plant; and
    interpreting a final outcome of the plant based on the set of features.

4. The method of claim 1:
    further comprising:
        dispatching the mover to autonomously navigate to the group of modules during the first time period;
        accessing a first set of module-level images of the first module captured by the mover at a second frequency that is less than the first frequency during the first time period;
        interpreting intermediate outcomes of the first set of plants, occupying the first module during the first time period, based on the first set of module-level images;
        writing intermediate outcomes of the first set of plants to the first set of plant records; and
    wherein deriving relationships between ambient conditions and final outcomes based on the corpus of plant records comprises deriving relationships between ambient conditions, intermediate outcomes, and final outcomes based on the corpus of plant records.

5. The method of claim 4, wherein writing intermediate outcomes of the first set of plants to the first set of plant records comprises, for each plant in the first set of plants:
    selecting a plant location in the first module;
    identifying a plant record associated with the plant location; and
    writing an intermediate outcome of the plant, interpreted from regions of the first set of module-level images corresponding to the plant location, to the plant record.

6. The method of claim 1:
    further comprising:
        accessing a set of water quality data captured by the mover via a probe inserted into the first module by the mover during the first time period; and
        writing the set of water quality data to the first set of plant records; and
    wherein deriving relationships between ambient conditions and final outcomes based on the corpus of plant records comprises deriving relationships between ambient conditions, water quality, and final outcomes based on the corpus of plant records.

7. The method of claim 6, wherein accessing the set of water quality data captured by the mover during the first time period comprises intermittently dispatching the mover to navigate to the grow area and sequentially sample water quality in modules in the group of modules at a second frequency different than the first frequency.

8. The method of claim 1:
wherein accessing the series of ambient conditions comprises accessing a series of ambient humidity data captured by the fixed sensor unit during the first time period,
wherein deriving relationships between ambient conditions and final outcomes based on the corpus of plant records comprises deriving a relationship between ambient humidity and final outcomes of plants grown in the facility, and
the method further comprising setting a target humidity range in the grow area based on the relationship between ambient humidity and final outcomes of plants grown in the facility.

9. The method of claim 8, further comprising:
estimating leaf areas of plants occupying modules in the grow area;
predicting a future humidity in the grow area at a future time based on a combination of leaf areas of plants occupying modules in the grow area and a plant transpiration model;
in response to the future humidity in the grow area at the future time exceeding the target humidity range, identifying a second module occupied by a second set of plants nearing a target outcome, wherein the second module is located in the grow area;
dispatching the mover to autonomously deliver the second module to the transfer station; and
triggering the transfer station to harvest the second set of plants from the second module.

10. The method of claim 1:
wherein interpreting the final outcome of the plant for each plant in the first set of plants comprises, for each plant in the first set of plants:
characterizing a final color, a final size, and a final geometry of the plant based on plant-level data of the plant captured by the transfer station during the second time period; and
calculating a viability score of the plant based on the final color, the final size, and the final geometry of the plant; and
wherein writing the final outcome of the plant to the plant record for each plant in the first set of plants comprises, for each plant in the first set of plants, writing the viability score of the plant to a plant record associated with the plant.

11. A method for monitoring growth of plants within a facility comprising:
during a first time period, dispatching a mover to autonomously navigate to a grow area within the facility;
accessing a first set of module-level data captured by the mover, at a first frequency, when the mover is proximal a first module occupying the grow area during a first period of time;
interpreting intermediate outcomes of a first set of plants occupying the first module during the first time period based on the first set of module-level data;
writing intermediate outcomes of the first set of plants to a first set of plant records associated with the first set of plants occupying the first module during the first time period;
during a second time period succeeding the first time period, dispatching the mover to autonomously deliver the first module from the grow area to a transfer station;
for each plant in the first set of plants:
interpreting a final outcome of the plant based on plant-level data captured by the transfer station while transferring the plant out of the first module during the second time period; and
writing the final outcome of the plant to a plant record, in the first set of plant records, associated with the plant; and
deriving relationships between intermediate outcomes and final outcomes of plants within the facility based on the first set of plant records.

12. The method of claim 11:
further comprising:
accessing a series of ambient conditions captured by a fixed sensor unit arranged proximal the grow area within the facility, wherein the series of ambient conditions are captured at a second frequency greater than the first frequency during a third time period preceding the second time period; and
writing the series of ambient conditions to a corpus of plant records associated with plants occupying a group of modules within the grow area based on known locations of modules within the grow area during the third time period, the corpus of plant records comprising the first set of plant records;
wherein deriving relationships between intermediate outcomes and final outcomes from the first set of plant records comprises deriving relationships between ambient conditions, intermediate outcomes, and final outcomes based on the corpus of plant records.

13. The method of claim 11:
wherein accessing the first set of module-level data captured by the mover comprises accessing a module-level image of the first module captured by the mover when the mover is proximal the first module during the first time period;
wherein interpreting intermediate outcomes of the first set of plants occupying the first module during the first time period based on the first set of module-level data comprises, for each plant in the first set of plants occupying the first module during the first time period:
identifying a first region of the module-level image depicting the plant;
extracting a first set of features from the first region of the module-level image; and
interpreting an intermediate outcome of the plant based on the first set of features; and
wherein interpreting the final outcome of the plant for each plant in the first set of plants comprises, for each plant in the first set of plants:
accessing a plant-level image of the plant captured by the transfer station while transferring the plant out of the first module during the second time period;
extracting a second set of features from the plant-level image of the plant; and
interpreting a final outcome of the plant based on the second set of features.

14. A method for monitoring growth of plants within a facility comprising:
aggregating global data captured by a fixed sensor unit arranged proximal a grow area within the facility, wherein the global data is captured at a first frequency during a grow period;

aggregating interim conditions of a first set of plants occupying a first module in the grow area, wherein the interim conditions are captured based on module-level data captured by a mover at a second frequency less than the first frequency while proximal the first module during a period of time;

dispatching the mover to autonomously deliver the first module to a transfer station;

interpreting outcomes of the first set of plants based on plant-level data captured by the transfer station while transferring plants out of the first module following conclusion of the grow period; and deriving relationships between global data, interim conditions, and outcomes from a corpus of plant records associated with plants grown in the facility.

15. The method of claim 14:

wherein aggregating global data captured by the fixed sensor unit during the grow period comprises aggregating ambient conditions measured by the fixed sensor unit at the first frequency during the grow period;

wherein deriving relationships between global data, interim conditions, and outcomes based on the corpus of plant records comprises deriving strengths of relationships between ambient conditions, measured at the first frequency, and outcomes of plants grown in the facility; and further comprising:
  generating a new grow schedule defining target ambient conditions for a new plant over a growth cycle and predicted to yield a target final outcome for the new plant based on strengths of relationships between ambient conditions and final outcomes of plants grown in the facility; and
  for a second module loaded with a second set of plants and occupying the grow area during a second grow period succeeding the grow period, autonomously adjusting actuators within the facility according to the new grow schedule based on ambient conditions measured by the fixed sensor unit during the second grow period.

16. The method of claim 14:

wherein aggregating global data captured by the fixed sensor unit during the grow period comprises:
  accessing a global image of a group of modules, the group of modules comprising the first module, the global image captured by the fixed sensor unit at a first time during the grow period;
  identifying a first region of the global image depicting the first module;
  extracting a first set of features from the first region of the global image;
  interpreting a global condition of the first set of plants at the first time based on the first set of features; and
  writing the global condition to a first set of plant records, in the corpus of plant records, associated with the first set of plants, wherein deriving relationships between global data, interim conditions, and outcomes based on the corpus of plant records comprises deriving relationships between the global condition, interim conditions, and outcomes based on the first set of plant records.

17. The method of claim 14, wherein aggregating interim conditions of the first set of plants comprises:
  accessing a module-level image of the first module captured by the mover when proximal the first module;
  for each plant in the first set of plants occupying the first module:
    identifying a second region of the module-level image depicting the plant;
    extracting a second set of features from the second region of the module-level image;
    interpreting an intermediate outcome of the plant based on the second set of features; and
    writing the intermediate outcome to a plant record, in the corpus of plant records, associated with the plant;

wherein interpreting outcomes of the first set of plants based on plant-level data captured by the transfer station while transferring plants out of the first module following conclusion of the grow period comprises interpreting final outcomes of the first set of plants based on plant-level data captured by the transfer station while transferring plants out of the first module following conclusion of the grow period; and wherein deriving relationships between global data, intermediate outcomes, conditions, and final outcomes based on the corpus of plant records comprises deriving relationships between the global data, interim conditions, and final outcomes based on the corpus of plant records.

18. The method of claim 14:

wherein interpreting outcomes of the first set of plants based on plant-level data captured by the transfer station comprises, for each plant in the first set of plants:
  accessing a plant-level image of the plant captured by the transfer station while transferring the plant out of the first module during a time period succeeding the grow period;
  extracting a third set of features from the plant-level image of the plant;
  interpreting a final outcome of the plant based on the third set of features; and
  writing the final outcome to a plant record, in the corpus of plant records, associated with the plant, wherein deriving relationships between global data, interim conditions, and outcomes based on the corpus of plant records comprises deriving relationships between the global data, interim conditions, and final outcomes based on the corpus of plant records.

19. The method of claim 14:

wherein aggregating global data captured by the fixed sensor unit during the grow period comprises:
  accessing a set of ambient air quality data captured by the fixed sensor unit during the grow period; and
  writing the set of ambient air quality data to a first set of plant records associated with the first set of plants occupying the first module located in the grow area during the grow period;

wherein aggregating interim conditions of the first set of plants during the period of time comprises:
  accessing a set water quality data captured by the mover via a probe inserted into the first module by the mover during a first time period; and
  writing a set of water quality data to the first set of plant records; and wherein deriving relationships between global data, interim conditions, and outcomes based on the corpus of plant records comprises deriving relationships between ambient air quality, water quality, and final outcomes based on the corpus of plant records comprising the first set of plant records.

20. The method of claim 14:

wherein interpreting outcomes of the first set of plants based on plant-level data captured by the transfer station while transferring plants out of the first module following conclusion of the grow period comprises intermediate outcomes of the first set of plants based on plant-level data captured by the transfer station while transferring plants out of the first module following conclusion of the grow period, the method further comprising:
- dispatching the mover to autonomously deliver a second module to the grow area, the second module occupied by a subset of the first set of plants transferred out of the first module by the transfer station following conclusion of the grow period;
- aggregating global data captured by the fixed sensor unit during a finishing period following conclusion of the grow period;
- dispatching the mover to autonomously deliver the second module to the transfer station; and
- interpreting final outcomes of the subset of the first set of plants based on plant-level data captured by the transfer station while transferring plants out of the second module following conclusion of the finishing period, wherein deriving relationships between global data, interim conditions, and outcomes based on the corpus of plant records comprises deriving relationships between global data captured during the grow period, global data captured during the finishing period, intermediate outcomes, and final outcomes based on the corpus of plant records of plants grown in the facility.

* * * * *